United States Patent
Ulmann et al.

(10) Patent No.: US 12,138,266 B2
(45) Date of Patent: Nov. 12, 2024

(54) FOLATE PREPARATIONS

(71) Applicant: APROFOL AG, Appenzell Steinegg (CH)

(72) Inventors: Martin Ulmann, Dachsen (CH); Gerd Wiesler, Lohn (CH); Hans Dutler, Zürich (CH)

(73) Assignee: Aprofol AG (CH)

( * ) Notice: Subject to any disclaimer, the term of this patent is extended or adjusted under 35 U.S.C. 154(b) by 700 days.

(21) Appl. No.: 17/256,456

(22) PCT Filed: Jul. 1, 2019

(86) PCT No.: PCT/EP2019/067644
§ 371 (c)(1),
(2) Date: Dec. 28, 2020

(87) PCT Pub. No.: WO2020/002714
PCT Pub. Date: Jan. 2, 2020

(65) Prior Publication Data
US 2021/0267982 A1   Sep. 2, 2021

(30) Foreign Application Priority Data
Jun. 29, 2018   (EP) ..................................... 18181019

(51) Int. Cl.
*A61K 31/519* (2006.01)
*A61K 9/00* (2006.01)
*A61P 17/00* (2006.01)

(52) U.S. Cl.
CPC .......... *A61K 31/519* (2013.01); *A61K 9/0014* (2013.01); *A61P 17/00* (2018.01)

(58) Field of Classification Search
CPC .............................. A61K 31/519; A61K 31/16
See application file for complete search history.

(56) References Cited

U.S. PATENT DOCUMENTS

| | | | |
|---|---|---|---|
| 2002/0150601 A1* | 10/2002 | Max ..................... | A61K 31/519 514/251 |
| 2004/0081668 A1 | 4/2004 | Puglia | |
| 2007/0258892 A1 | 11/2007 | Tallberg | |
| 2014/0274982 A1 | 9/2014 | Bakan et al. | |
| 2016/0207925 A1* | 7/2016 | Fracchia ............. | C07D 475/04 |
| 2017/0014358 A1 | 1/2017 | Tuffley | |
| 2017/0273984 A1 | 9/2017 | Cheng et al. | |

FOREIGN PATENT DOCUMENTS

| | | | | |
|---|---|---|---|---|
| JP | 2002212077 A | 7/2002 | | |
| JP | 2007520532 A | 7/2007 | | |
| JP | 2010280738 A | 12/2010 | | |
| JP | 2016501205 A | 1/2016 | | |
| JP | 2016515525 A | 5/2016 | | |
| JP | 2017526699 A | 9/2017 | | |
| WO | 8804927 A1 | 7/1988 | | |
| WO | WO88/04927 | * | 7/1988 | ............. A61K 31/16 |
| WO | WO95/15148 | * | 1/1994 | ............. A61K 31/16 |
| WO | 9515148 A1 | 6/1995 | | |
| WO | 2009103334 A1 | 8/2009 | | |
| WO | WO2009/103334 | * | 8/2009 | ............. A61K 31/16 |
| WO | 2010102214 A2 | 9/2010 | | |
| WO | WO2010/102214 | * | 9/2010 | ............. A61K 31/16 |
| WO | 2014177273 A1 | 11/2014 | | |

OTHER PUBLICATIONS

International Search Report and Written Opinion for International Application No. PCT/EP2019/067644, dated Oct. 4, 2019, 11 pages.
Khan et al., "Basics of Pharmaceutical Emulsions: A Review", African Journal of Pharmacy and Pharmacology, Dec. 30, 2011, vol. 5(25), pp. 2715-2725.
Japanese Notification of Reasons for Rejection for Japanese Application No. 2020-572859, dated Jun. 9, 2023 with translation, 7 pages.

* cited by examiner

*Primary Examiner* — Paul V Ward
(74) *Attorney, Agent, or Firm* — Buchanan Ingersoll & Rooney PC

(57) ABSTRACT

The present invention relates to preparations of folate salts and their topical use for the treatment of epithelial tissue irritations and skin disorders.

19 Claims, 27 Drawing Sheets

Day 0　　　Day 5　　　Day 15　　　5 months 9 months

FOLATE PREPARATIONS

CROSS-REFERENCE TO RELATED APPLICATIONS

This application is a U.S. National Stage application of PCT International Application No. PCT/EP2019/067644, filed Jul. 1, 2019, which claims priority of European Application No. 18181019.3, filed Jun. 29, 2018, the disclosures of which are incorporated herein by reference in their entirety.

BACKGROUND

The present invention relates to preparations of folate salts and their use in topical treatment of irritations and disorders, in particular skin irritations and disorders.

Folic acid is a widely present growth factor having the character of a vitamin. Reduced folic acid is necessary for cells to divide properly as it is required for producing the genetic material DNA. As a result, cells and tissues that divide rapidly such as skin cells and intestinal cells are directly impacted by folic acid status.

In nature folates are present in the form of reduced folates carrying mono- or polyglutamate groups. Human metabolism is not capable of forming these folate compounds. Hence, folates have the character of a vitamin. De-novo synthesis of folate compounds only occurs in micro-organisms and plants. Folic acid itself is biologically inactive and must be enzymatically reduced via dihydrofolate reductase to 7,8-dihydrofolic acid and further to 5,6,7,8-tetrahydrofolic acid. Tetrahydrofolic acid (THF) is the biologically active form of folic acid. THF serves as carrier for $C_1$ units wherein the transfer is achieved via 5-Methyl-tetrahydrofolate, 5,10-Methylene-tetrahydrofolate, 5-Formyl-tetrahydrofolate, 5-Formimino-tetrahydrofolate, 10-Formyl-tetrahydrofolate and 5,10-Methenyl-tetrahydrofolate, respectively. $C_1$ units are for instance required in the synthesis of purine nucleotides and Desoxythymidin-5'-monophosphate.

Numerous causes may promote or lead to a folate deficiency. For instance, an increased need for folate as seen during pregnancy may eventually lead to a status of folate deficiency. Further, malabsorption of folate from food due to coeliac disease, intake of anti-metabolites such as methotrexate, aminopterin in cancer therapy used as competitive inhibitors of dihydrofolate reductase, and alcohol abuse may cause folate deficiency. Also, genetically founded malfunctions in one or more of the enzymes of folate metabolism may lead to folate levels below normal. In addition, inflammatory conditions may cause decreased folate levels which may be due to higher demand of present folate and/or malabsorption of folate needed in repair processes of the tissue affected by the inflammation. In the skin, a lack of folate can lead to a condition called seborrheic dermatitis and may be related to vitiligo (loss of skin pigment).

The consequences of a deficiencies in the folate status are numerous as are the roles folate plays in metabolism, e.g. there occur disruptions in the amino acid and nucleic acid metabolism. The latter being directly linked to the process of cell division. In tissue which shows a fast cell division such as bone marrow this may lead to megaloblastic anemia or thrombocytopenia.

A positive effect of folate in the decrease of homocysteine levels (known as one of the risk factors for cardiovascular diseases) could be shown in clinical trials, wherein a typical daily intake of 400 µg folate is necessary to achieve a positive effect, i.e. a reduction of homocysteine levels in blood.

A sufficient supply of folates wherein folates are mainly comprised in leafy vegetables, cereals and liver proves quite difficult as the folates are susceptible to heat and light. Thus, the supply of folate to healthy individuals via nutrition does not necessarily guarantee a sufficient supply. This is on the contrary seen as the main cause for individuals having a decreased folate status. The uptake of folate via other routes, e.g. via skin, as well as the uptake in the skin itself is not yet fully clear.

SUMMARY

There is thus an ongoing need for alternative methods of use of folate and preparations of folate which provide for a good uptake of folate in tissues.

In a first aspect of the invention there is provided a novel use of folate as an active agent for the prevention and/or treatment of skin irritations and skin disorders.

Another object of the present invention is to provide folate preparations where the folate is readily absorbed in the tissue.

The objects are achieved by a method of treating epithelial tissue irritations and disorders, comprising topically administering a preparation comprising at least one folate to a patient in need thereof, and by a preparation comprising a physiologically effective amount of at least one folate salt having a cation selected from the group consisting of arginine, choline, acetylcholine, 1,1-dimethylbiguanidine, phenylethylbiguanidine, glucosamine, and dimethylaminoethanol and one or more customary compounds for forming a support matrix. Preferred embodiments of the invention are disclosed in the detailed description that follows.

DETAILED DESCRIPTION

According to the present invention preparations comprising at least one folate are used for the treatment of epithelial tissue irritations and disorders, preferably skin irritations and skin disorders. The use of the preparation is a topical use. Preferably, the skin irritation or skin disorder is an inflammatory skin disorder. The inflammation may either be acute or chronic. The latter referring to a prolonged inflammatory state. An example for a chronic inflammatory disease is psoriasis. Further, treatment of chronic wounds is also feasible by topical treatment with folate preparations. As chronic wounds are considered wounds that do not heal within an expected period, e.g. within 8 to 12 weeks. Chronic wounds seem to be detained in one or more of the phases of wound healing. An example for a disorder of epithelial tissue at the eye is the dry eye syndrome (DES), also known as keratoconjunctivitis sicca (KCS).

A folate preparation according to the present invention comprises a physiologically effective amount of at least one folate salt. The cation of the folate salt is selected from the group which consists of arginine, choline, acetylcholine, 1,1-dimethylbiguanidine, phenylethylbiguanidine, glucosamine and dimethylaminoethanol. The preparation further comprises customary compounds for the formation of a support matrix.

The cation of the folate salt may also be selected from the group consisting of calcium, magnesium, sodium, and zinc.

The cations selected from the group consisting of arginine, choline, acetylcholine, 1,1-dimethylbiguanidine, phenylethylbiguanidine, glucosamine and dimethylaminoethanol are preferred.

In a further embodiment the at least one folate of the folate salt is selected from the group consisting of the following folate compounds, 5-formyl-(6RS)-tetrahydrofolic acid, 5-formyl-(6S)-tetrahydrofolic acid, 10-formyl-(6R)-tetrahydrofolic acid, 5-methyl-(6RS)-tetrahydrofolic acid, 5-methyl-(6S)-tetrahydrofolic acid, (6S)-tetrahydrofolic acid, 5,10-methylene-(6R)-tetrahydrofolic acid, 5-methyl-10-formyl-(6S)-tetrahydrofolic acid, and 5,10-diformyl-(6S)-tetrahydrofolic acid.

The preparation comprises in another embodiment further pharmaceutically active compounds. These compounds are preferably selected from the group consisting of arginine, arginine ester, choline, acetylcholine, dimethylaminoethanol, vitamins of the B complex, and vitamin D, in particular vitamin $D_3$.

In a further embodiment the preparation further comprises at least one compound selected from the group consisting of sodium gluconate, potassium gluconate, glycerophosphate disodium salt, and glycerophosphate dipotassium salt.

The folate preparation according to the present invention comprises a concentration of 0.01 weight-% to 2.5 weight-% of the folate compound based on the total weight of the folate preparation in a multiphase mixture with a polar non-aqueous phase or with an aqueous phase.

Further, folate preparations may comprise a higher amount of the folate compound of up to 5 weight-% or even up to 10 weight-% based on the total weight of the folate preparation. The folate compound may be dissolved in an aqueous or in a non-aqueous solvent, the latter being for instance glycerol. The minimal amount of the folate compound is 0.01 weight-% based on the total weight of the folate preparation.

In another embodiment the preparation comprises thoroughly mixed phases. Phase A comprises an oil. Phase B comprises glycerol and an emulsifier. The phase C comprises an aqueous folate composition comprising a physiologically effective amount of a folate salt, and optionally at least one compound selected from the group consisting of sodium gluconate, potassium gluconate, glycerophosphate disodium salt and glycerophosphate dipotassium salt. It may optionally comprise further compounds such as a pharmaceutically acceptable buffer, e.g. tris(hydroxymethyl)-aminomethan (TRIS), and a pharmaceutically acceptable antioxidant, e.g. glutathione. Optional phase D comprises one or more matting agents.

A folate preparation according to the present invention preferably comprises in phase C 0.1 mg to 1000 mg at least one folate salt selected of the group consisting of calcium, magnesium, sodium, zinc, arginine, choline, acetylcholine, 1,1-dimethylbiguanidine, phenylethylbiguanidine, and dimethylaminoethanol salt of the folate per milliliter of a polar solvent. Polar solvents are for instance water, methanol, ethanol, n-propanol, isopropanol, glycerine, dimethylsulfoxide. Mixtures of such polar solvents may also be used. Arginine, choline, acetylcholine, 1,1-dimethylbiguanidine, phenylethylbiguanidine, glucosamine and dimethylaminoethanol salt of the folate are preferred.

In another embodiment the phase C comprises for one mole of the folate salt 0.8 to 10 molar sodium gluconate or potassium gluconate. If phase C comprises glycerophosphate disodium salt or glycerophosphate dipotassium salt, these salts are preferably present in a concentration of 0.4 to 5 molar.

Preferably, preparations according to the present invention comprise in phase A an oil consisting of a medium-chain triglycerol. Fatty acid of such medium-chain triglycerols have a chain-length in the range of $C_6$ to $C_{12}$. Most preferred is the oil of caprylic/capric acid triglycerol. Further, it may optionally comprise a dicarbonic acid alcohol. The dicarbonic acid has a chain length in the range of $C_2$ to $C_{10}$ and the alcohol is selected of the group consisting of methyl, ethyl, isopropyl, propyl, butyl, pentyl alcohol.

Emulsifiers used in phase B of preparations preferably have HLB value equal or greater than 5. The hydrophilic-lipophilic balance of a surfactant is a measure of the degree to which it is hydrophilic or lipophilic, determined by calculating values for the different regions of the molecule, as described by Griffin in 1954. Griffin's method for non-ionic surfactants as described in 1954 works as follows: $HLB=20\times M_h/M$, wherein $M_h$ is the molecular weight of the hydrophilic portion of the compound and M is the total molecular weight of the compound. An HLB value of 0 corresponds to a completely lipophilic/hydrophobic molecule, and a value of 20 corresponds to a completely hydrophilic/lipophobic molecule. An emulsifier having HLB value in the range of 8 to 16 is suitable for stabilizing oil in water (o/w) emulsions.

A preferred emulsifier is a sucrose ester, wherein the fatty acids have chain length in the range of $C_{14}$ to $C_{20}$. Such sucrose esters must have a HLB value equal or greater than 5. Most preferred is the emulator sucrose stearate.

In another embodiment the preparation according to the present invention is used for the treatment of skin irritations and skin disorders. The use is preferably a topical use. The folate preparations may be used for the treatment of inflammatory skin disorders, in particular for psoriasis.

Further, the folate preparations may also be used for the treatment of wounds, in particular chronic wounds. A wound is a type of injury which happens relatively quickly in which skin is torn, cut, or punctured (an open wound), or where blunt force trauma causes a contusion (a closed wound). In pathology, it specifically refers to a sharp injury which damages the dermis of the skin.

In another aspect, the sodium and potassium salts of gluconate and glycerophosphate can be used as permeation enhancers increasing the permeation of the folate salt into the skin.

For a further understanding of the invention, reference is made to the following examples, taken in connection with the accompanying figures which show:

EXAMPLE 1

Figure 1:
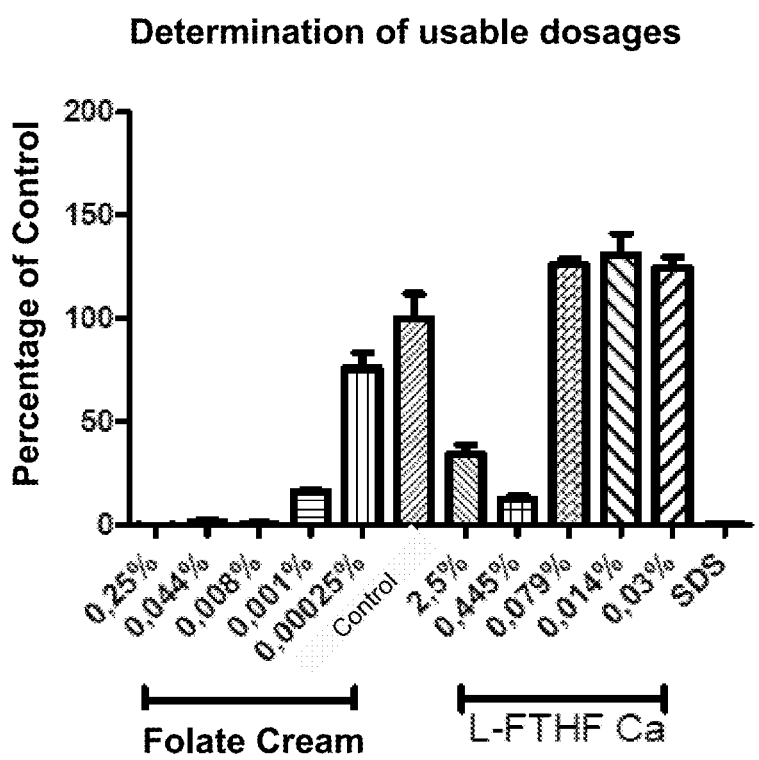
FIG. 1 shows the determination of usable dosages of test substances or preparations folate cream and L-FTHF.

An exemplary cream comprising a calcium salt of levofolinate comprises the following compounds:

Cream preparation 1

| | INCI-Name | Weight-% |
|---|---|---|
| Phase A | Caprylic/Capric Triglyceride | 51.800 |
| Phase B | Glycerine | 30.000 |
| | Sucrose Stearate | 2.000 |
| Phase C | Calcium Levofolinate | 0.100 |
| | Natrium Gluconate | 0.100 |
| | water | 9.800 |
| | Perfume | 0.200 |
| Phase D | Silica (matting agent) | 6.000 |
| | Total | 100.00 |

Cream preparation 2

| | INCI-Name | Weight-% |
|---|---|---|
| Phase A | Caprylic/Capric Triglyceride | 40.000 |
| | Diisopropyl Adipate | 3.000 |
| Phase B | Glycerine | 41.000 |
| | Sucrose Stearate | 2.000 |
| Phase C | Calcium Levofolinate | 0.250 |
| | Natrium Gluconate | 0.250 |
| | water | 9.500 |
| Phase D | Silica (matting agent) | 4.000 |
| | Total | 100.00 |

EXAMPLE 2: SCRATCH ASSAY

To examine the effect of different folate preparations on wound healing the in vitro model Scratch Assay was employed. This in vitro model comprises the defined injuring of a closed cell layer and the subsequent regrowth of the cells to a closed layer in the presence of the test-substance compared to appropriate controls, i.e. (untreated) cells with no test-substance present.

The experimental procedure for the Scratch Assay was as follows: The employed cells are primary keratinocytes of human skin (C-12005, Promocell, Heidelberg, Germany). At first, the dosage of the test-substances which does not exert a negative effect on the cells such as decreased cell viability. Three different dosages were then used for the Scratch Assay. Further, cells were cultivated in growth-limiting medium in order to show a possible growth promoting effect of the test substances. For the medium used (C-20011, Promocell, Heidelberg, Germany) a growth limitation could be achieved by either the omission or dilution of epidermal growth factor (EGF) or of a complex mixture of undefined factors derived from blood BPE). Usually, growth-limiting medium was achieved by the omission of EGF. For the actual Scratch Assay keratinocytes were cultivated in appropriate cell culture plates (6-well plates, 657160, Greiner BioOne, Frickenhausen, Germany) bearing position markings. Cells were grown to a closed monolayer. Then, cells were scratched with pipette tip along the position markings, thereby generating a cell free area (scratch, injury). Cell monolayers were washed to remove partially detached cells and then covered with medium comprising the test-substances in appropriate dosages. Regrowth of the cells into the cell free area was observed over time at 0 h, 6 h and 24 h and photographically documented at these times. Analysis was done by marking and calculating the cell-free area (software ImageJ) and comparing the calculated areas at the different time point. This allowed a conclusion on the growth rate in relation to the untreated controls (cell culture medium without any test-substance). For every dosage of the test-substances three replicates were done. The whole test was done twice.

Test-Substances:

| | Label | Remark | |
|---|---|---|---|
| 1 | Folate Creme | | Creme |
| 2 | L-FTHF Calcium | 252.6 | mg yellowish powder |
| 3 | Sodium Gluconate | 251.4 | mg white powder |
| 4 | L-MTHF di choline | 251.7 | mg white powder |
| 5 | L-FTHF di arginine | 250.8 | mg white powder |
| 6 | L-FTHF Calcium | 50.3 | mg yellowish powder |
| 7 | Sodium Gluconcate | 51.2 | mg white powder |
| 8 | L-MTHF di choline | 50 | mg white powder |
| 9 | L-FTHF di arginine | 50.4 | mg white powder |

Instructions for Solving the Samples

Solutions for the assays were prepared as follows:

L-FTHF Calcium (levoleucovorin calcium, calcium levofolinate, 5-formyl-(6S)-tetrahydrofolic acid calcium salt) (2.5%): mix 125 mg L-FTHF Ca and 125 mg sodium gluconate and dissolve with 4.25 g bidistilled water.

L-MTHF (2.5%): add 125 mg L-MTHF di choline salt (5-methyl-(6S)-tetrahydrofolic acid di choline salt) and dissolve with 4.875 g bidistilled water.

L-FTHF (2.5%): add 125 mg L-FTHF di arginine salt (5-formyl-(6S)-tetrahydrofolic acid di L-arginine salt) and dissolve with 4.875 g bidistilled water.

Folate cream (0.25% calcium levofolinate): the folate cream was used as delivered by the manufacturer and stored in the refrigerator.

In a preliminary experiment, the usable dose was determined. Because the cultures for the scratch assay were monolayer cell cultures that are significantly more sensitive than organotypic skin models used for bioavailability, it was not possible to treat these cell cultures with the undiluted solutions and preparations.

For this test, the keratinocytes were seeded on 96-well plates and incubated with five dilutions of the solutions or the cream for 24 h. Subsequently, a vital dye was added and finally, the colour change caused by the conversion of the vital dye in living cells was photometrically quantified.

Figure 2:
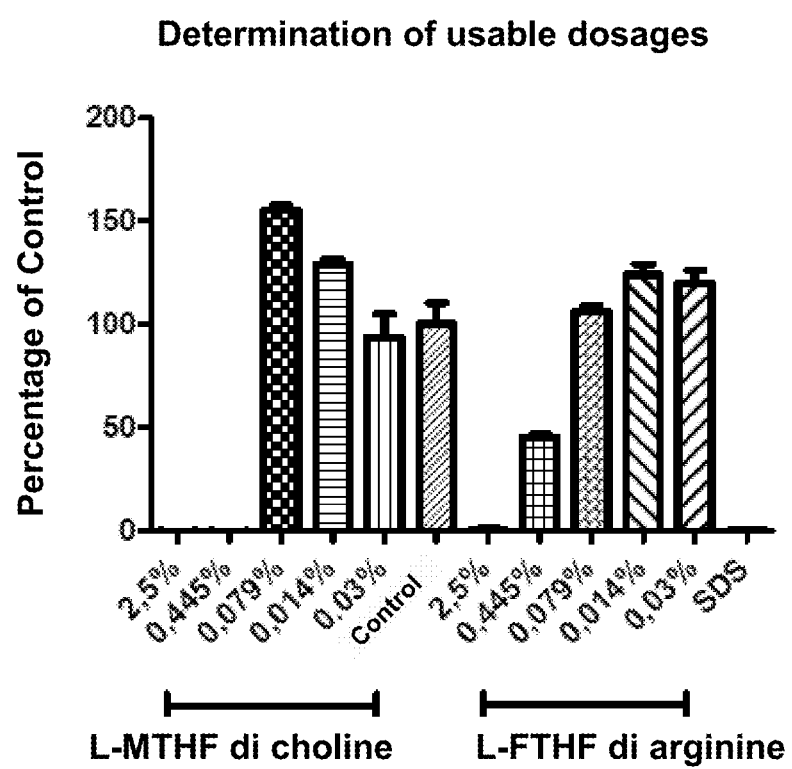
FIG. 2 shows the determination of usable dosages of test substances L-MTHF di choline and L-FTHF di arginine.

FIG. 1 and FIG. 2 show the determination of the usable dosage of the test substances. Cytotoxicity test with keratinocytes in monolayer culture after conversion of the vital dye MTT by living cells. The concentration data are based on the undiluted solutions or the cream (=100%). Treatment time=24 h. Untreated cultures served as negative controls. SDS served as a positive control ("dead control"). N=6+ SEM According to the results of the dose determination the folate cream could be used from a concentration of 0.00022% (viability=70% of the control). L-FTHF Ca could be used from a concentration of 0.13%. L-MTHF di choline could be used from a concentration of 0.14% and L-FTHF di arginine from a concentration of 0.12%. IC70 values were calculated by nonlinear regression (Hill Slope, GraphPad Prism 5.04). The term IC70 denotes the concentration at which the viability of the treated cell culture is reduced to 70% of the untreated control. IC70 is often referred to as the border between toxicity and non-toxic effect.

Also, in preparation for the Scratch Assay, it was examined whether the growth rate of the keratinocytes could be influenced. Media such as the serum-free culture medium used cause possibly optimum growth of the respective cells and possibly make further acceleration of growth impossible in this case. However, it was found that the medium used did not lead to the maximum proliferation rate of the cells (see FIG. 3). Thus, further experiments could be carried out with the unchanged standard medium.

For this study, keratinocytes were seeded diluted in 96-well plates. 24 hours after sowing, the standard medium was replaced by media of different calcium concentrations. 24 hours later, the number of living cells was determined by the respective turnover of a vital dye (MTT, 3-(4,5-dimethylthiazol-2-yl)-2,5-diphenyltetrazolium bromide).

Figure 3:
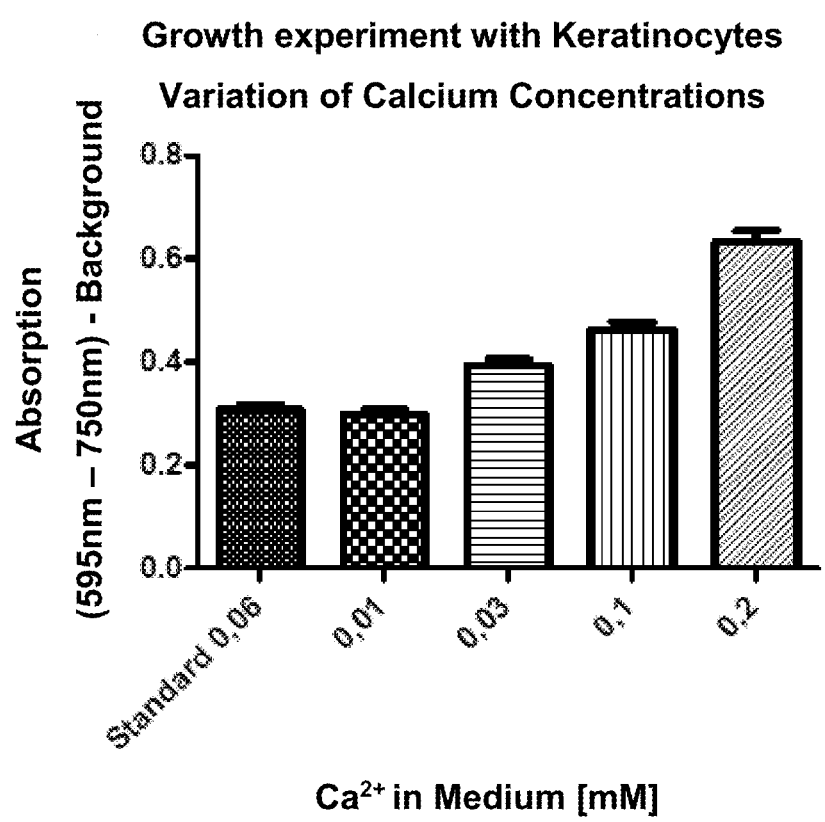
FIG. 3 shows the growth of keratinocytes at different calcium concentrations of the medium.

FIG. 3 shows growth experiment with keratinocytes. The variation in the calcium content of the medium resulted in part in faster growth. N=6+SEM.

This showed that an increase in the growth rate compared to cells cultivated in the standard medium is possible. Therefore, the standard medium was chosen as the basis for the supplementation in the Scratch Assay, since a depletion of the medium was not necessary in order to be able to show a growth acceleration. The standard medium also served as a control. As an additional control, bovine serum albumin (FBS) was added to the standard medium as it was expected that the growth factors it contained would accelerate the growth of keratinocytes and thus provide another reference.

Figure 4:
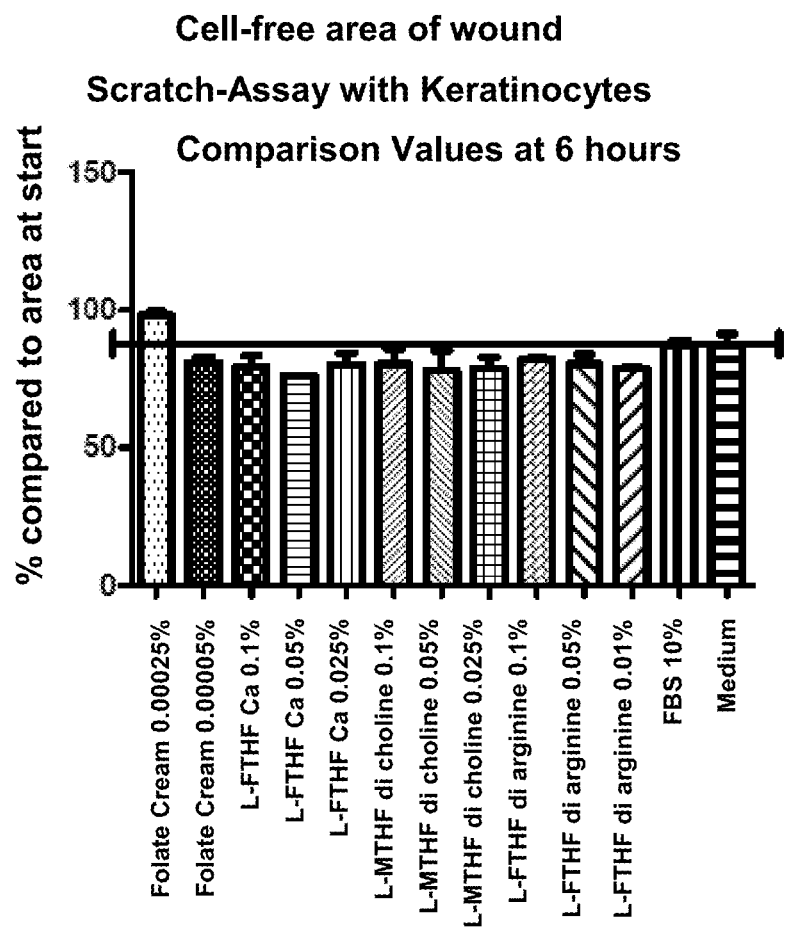
FIGS. 4, 5, 5A, 5B and 5C show results of the scratch assay.
Figure 5:
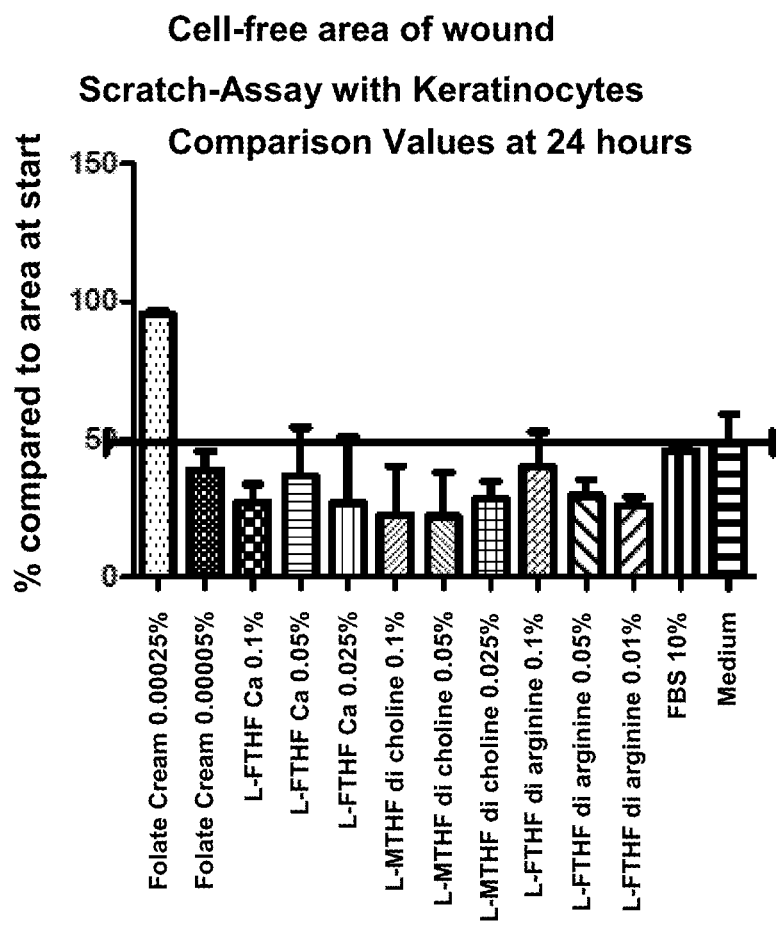

FIGS. 4 and 5 show the cell-free area of the induced scratch after 6 h or 24 h. The measured values were expressed as a percentage of the starting area of the respective treatment group. The line indicates the level of control (=standard medium). The smaller the bars, the faster the scratch, i.e. the cell free area was regrown with cells. For each treatment group, three concentrations were tested in three separate cultures (N=3)+SEM.

After 6 hours, no significant increase has yet been achieved, the treatment groups differ only slightly. After 24 h, it can clearly be seen that the folic acid solutions promote growth better than the standard medium and as the FBS control. The folate cream surprisingly hindered growth in the two higher concentrations. The highest concentration even led to the death of the cultures (bars not shown). This was not expected, as only a slight toxic effect was observed after the pretest for the highest concentration. This is probably a methodological problem because the stress caused by the injury is likely to increase the sensitivity of the culture. The folate solutions promote growth in a similar manner. The only thing that stands out is that L-FTHF di arginine (green) promoted dose-dependent reversal of "healing". However, since the differences are not significant, this result may have occurred accidentally.

Overall, the differences in wound area growth are not significant between the treated groups, which was probably due to the relatively large variation between the triplicates of a treatment group.

Figure 5A:
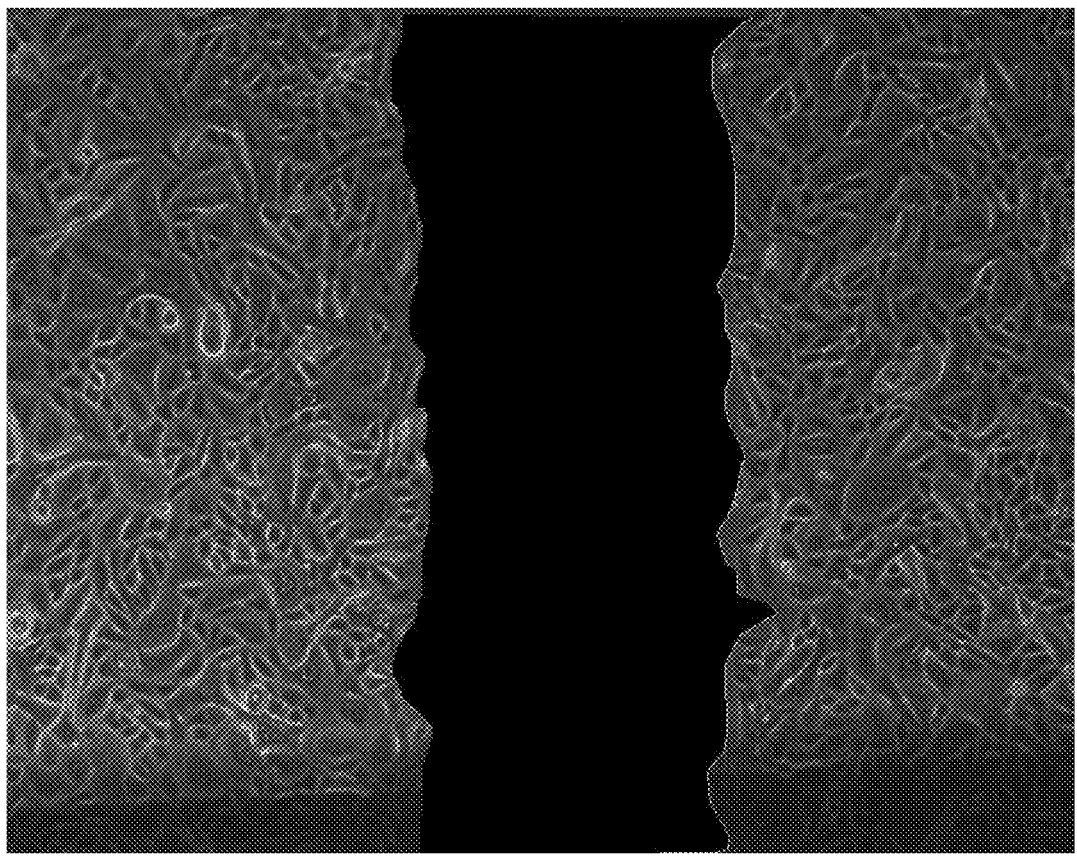
Figure 5B:
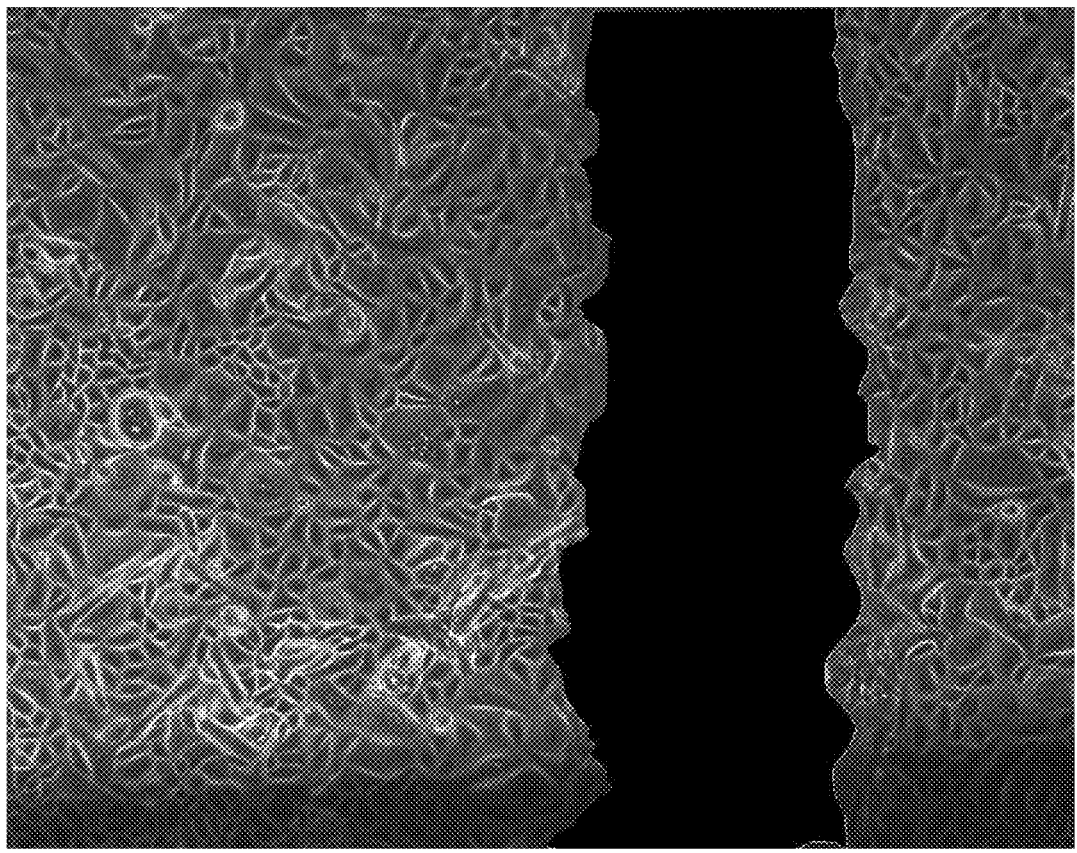
Figure 5C:
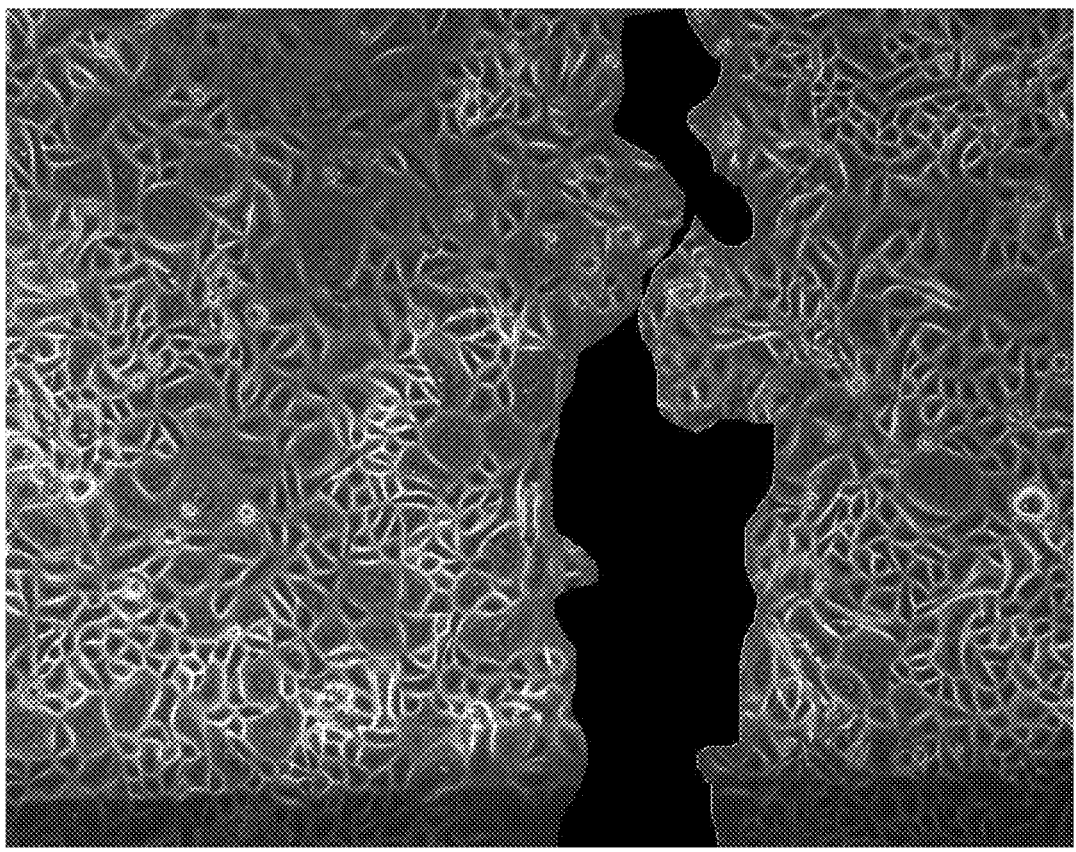

FIGS. 5A, 5B and 5C show the photographs taken for L-MTHF 0.1% from left to 0 h, after 6 h and after 24 h. The drawn line indicates the free wound surface as determined for the analysis program. After 6 h hardly any surface is overgrown after 24 h it becomes difficult to mark a cell-free area.

EXAMPLE 3: BIOAVAILABILITY

In order to test the bioavailability in tissues such as skin, reconstructed skin models (epiCS, CS-1001, CellSystems, Troisdorf) were used which are generated from primary human keratinocytes. These models show a barrier very similar to human skin. They are regularly used as test models for the approval-relevant determination of corrosive or irritating effects of cosmetic raw materials. The skin models can usually be treated with finished products, as they are intended for use by the consumer. Nevertheless, before the skin models are treated with the test products, an assessment of the tolerability of the models is made to avoid overdosing.

The skin models were cultured on a porous membrane as mentioned above. The skin cells growing on it separate an apical compartment (with the skin model) from a basal compartment (with the nutrient medium). Mass transport from the apical to the basal compartment is thus almost exclusively possible through the cells. The only alternative to this is paracellular diffusion, which however, due to the functional tight junctions, is only possible for a few molecules and to a very limited extent. To determine the bioavailability of the products, the barrier is checked for leaks before use by means of resistance measurements. Models with a significantly below-average electrical resistance between the apical and the basal part are not used in the experiment. Suitable skin models are then treated topically with the test products. After 4 h, 8 h and 24 h, samples of the medium were taken in the basal part of the models to check for the presence and concentration of folates. Each test product and controls are tested at a concentration of three replicates each. The studies were repeated to obtain results from two independent runs. The determination of the folate contents of the media samples was started with the analysis of the 24 h values. Since these already contained folate, further time points were subsequently examined in order to be able to image a kinetics of the uptake, if necessary.

The analysis of the media samples was carried out by way of a LC/MS method established at a commercial service provider. The sensitivity of the method is in the range of 1 nmol/L. Before the start of the investigations, an estimate of the feasibility or a preliminary test was carried out in order to be able to assess the suitability of the method. The sensitivity of the method proved to be sufficient for the analysis of the bioavailability.

In the preliminary experiment, 100 µL of the solubilized test substances which were the same as described in Example 2 were applied topically to each of three skin models. On three models, only 100 µL of water was applied. The skin models have a surface of 0.6 cm² each. After 24 h incubation, samples of the medium were removed from the models and frozen for the preliminary analysis. The models were then washed and incubated with a vital dye (Resazurin) to determine the number of living cells in the models. This was done to determine whether the treatment leads to a negative effect on the cells, which of course would also impair the barrier function of the skin models.

Figure 6:
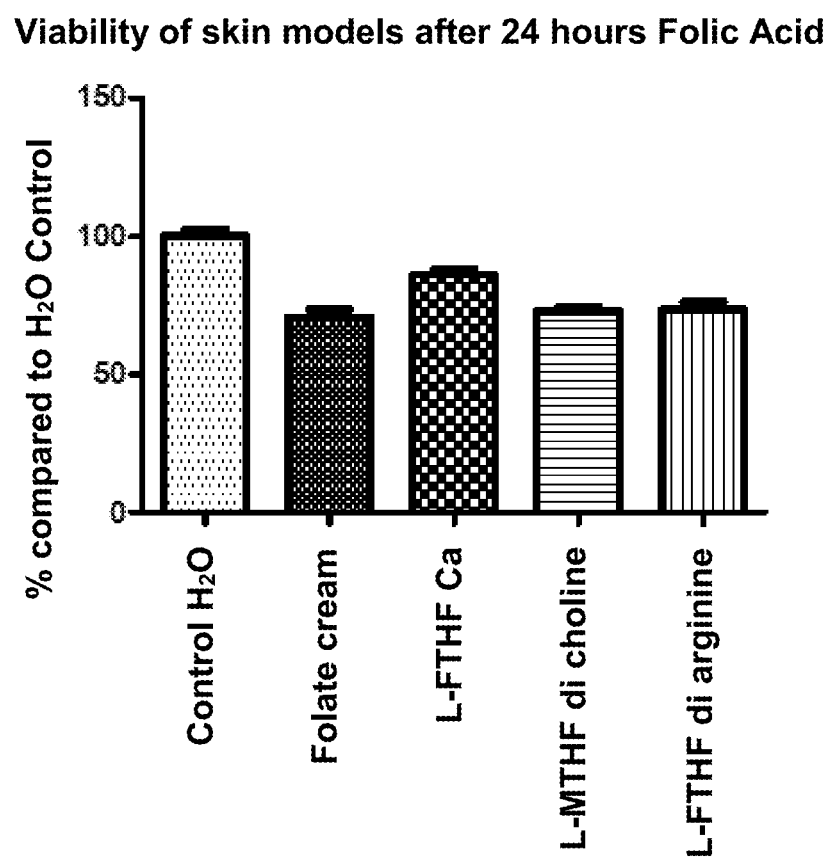
FIGS. 6 and 7 show results of cell viability after exposure to folic acid.
Figure 7:
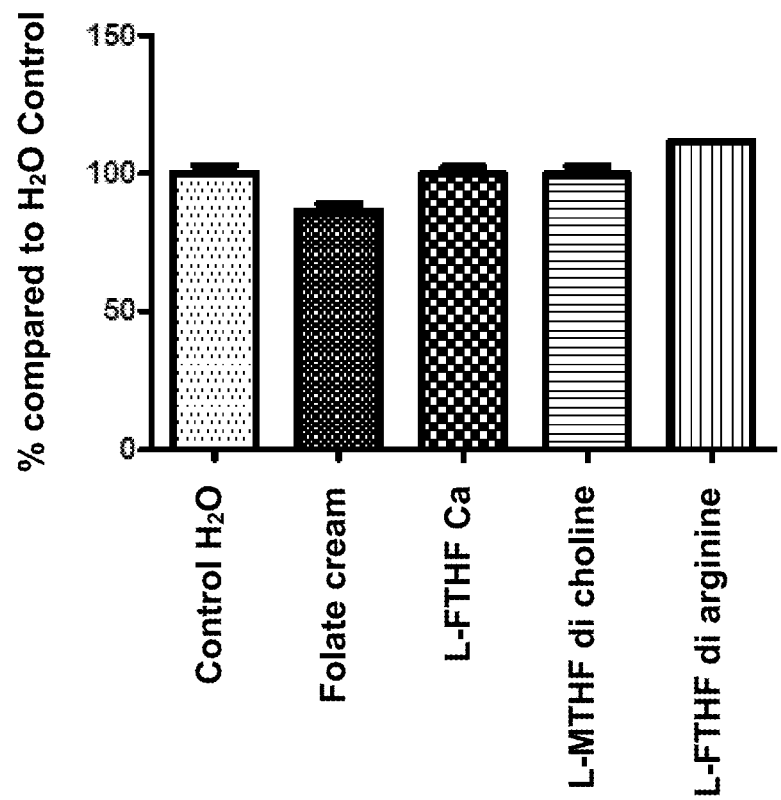

FIGS. 6 and 7 show the relative vitality of the skin model cells after 24 h topical treatment with 100 µL each of the test substances or water. The fluorescence values of the live dye (Resazurin) were normalized to the control (=100%). Results of each run with N=3+SEM.

It was found that the viability of the skin models was not adversely affected by the treatment in the run. With three of the test substances the treatment even seems to lead to a slightly increased vitality compared to the control. In the second passage, a slight decrease in viabilia following treatment with the folate cream is observed in 86% of the control. However, a decline of this low magnitude is not considered to be a toxic effect. The models were thus not significantly affected by the treatment in their viability. It is therefore to be assumed that the barrier function of the skin models is not impaired. The models could therefore be treated with the undiluted solution or cream 24 h. Compared to the test for irritating effects according to OECD TG 439, where the models are treated with the test substance for only 15 minutes, treatment over 24 hours is far more challenging. Thus, for the tested solutions and the cream, a very good compatibility for the human skin can be assumed.

Since the preliminary analysis of some test samples showed that a very strong folate signal could be measured which might cause problems for the separation columns during the analysis, a dilution of the test samples before analysis became necessary. In addition, the topically applied amount was reduced to 50 μL each. In addition, in the main experiment, the lower compartment was not filled with medium (contains folic acid) but with 1 mL Hank balanced salt solution (without folic acid). Following a total of 24 hours incubation with the test substances, the skin models were again incubated with Resazurin to. To be able to determine a possibly reduced vitality of the models. In the main trial, two independent passes were completed.

Figure 13:
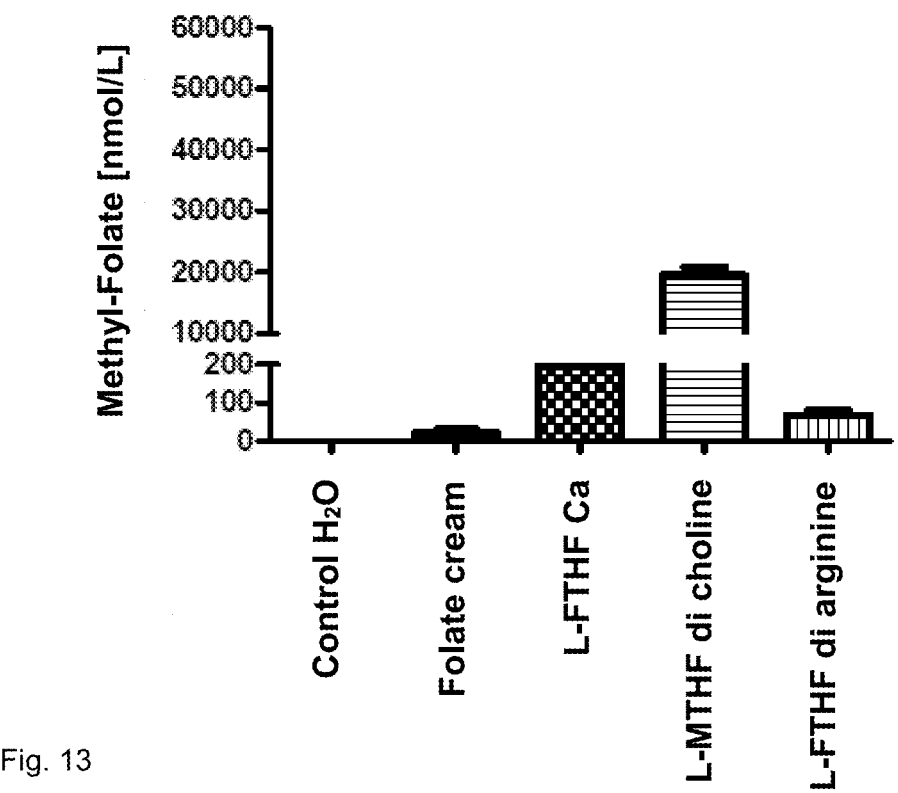
Figure 14:
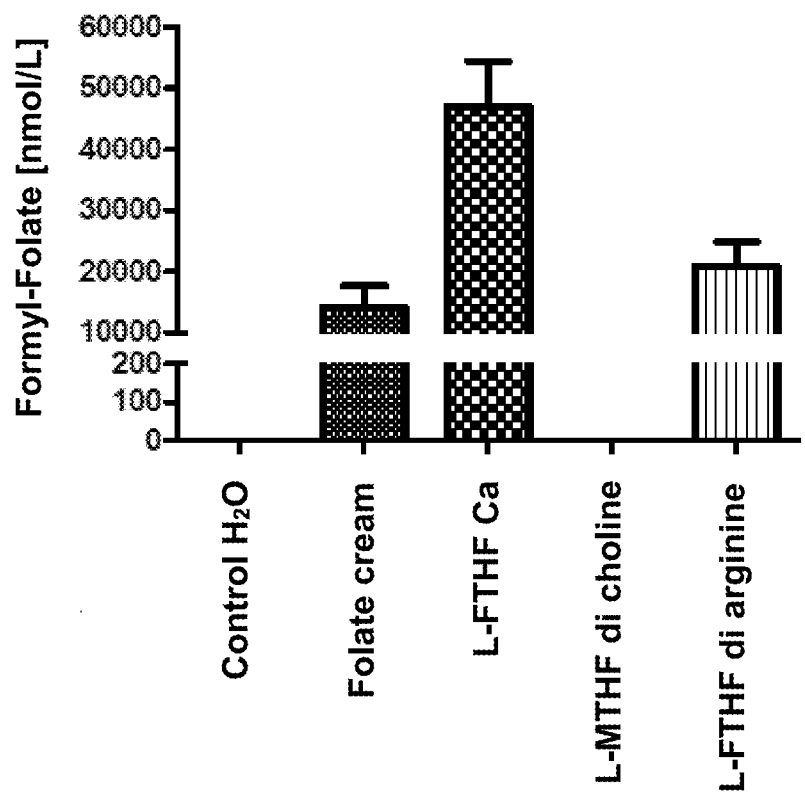
Figure 15A:
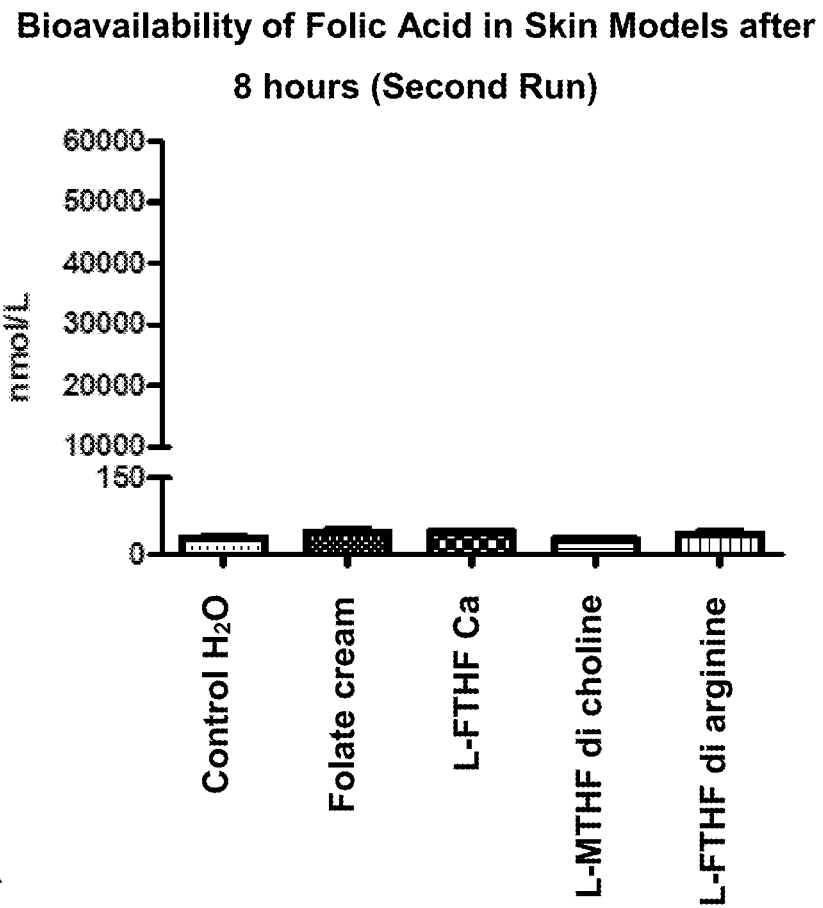
Figure 15B:
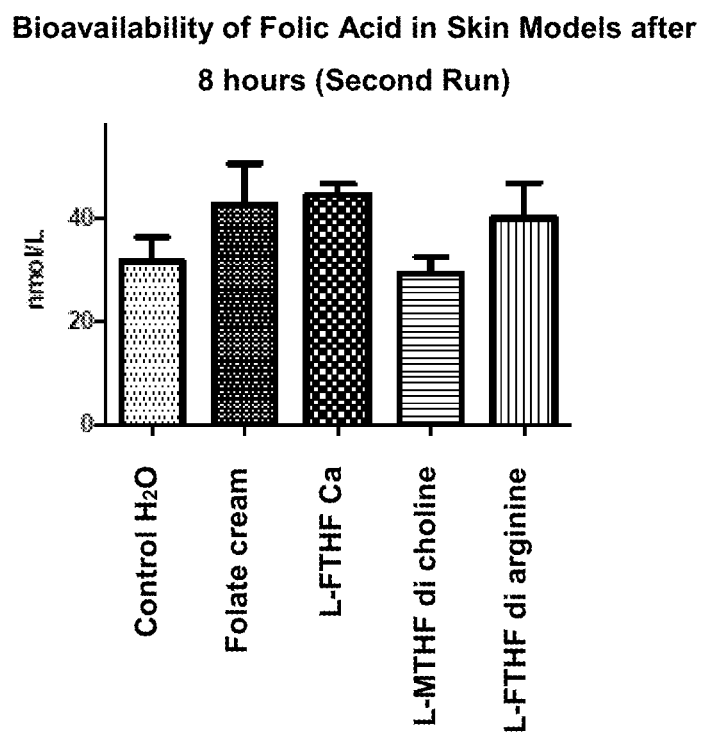
Figure 16:
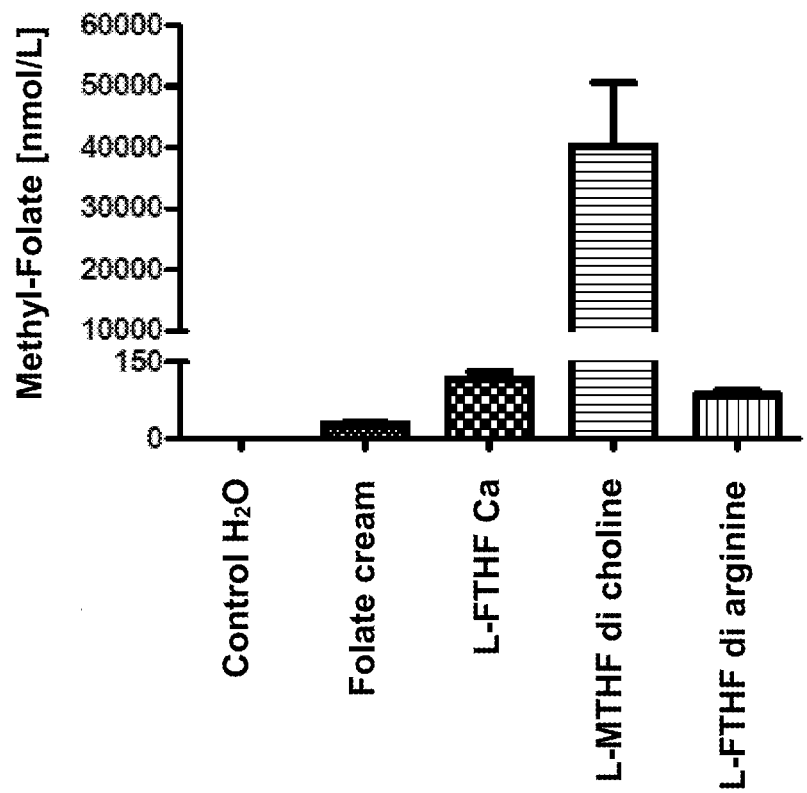
Figure 17:
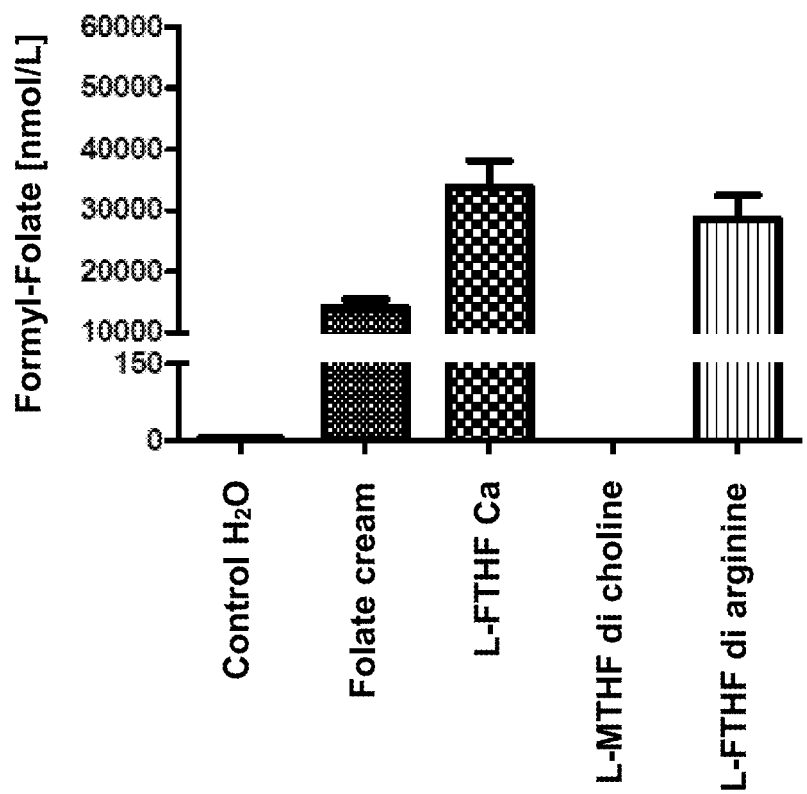
Figure 21:
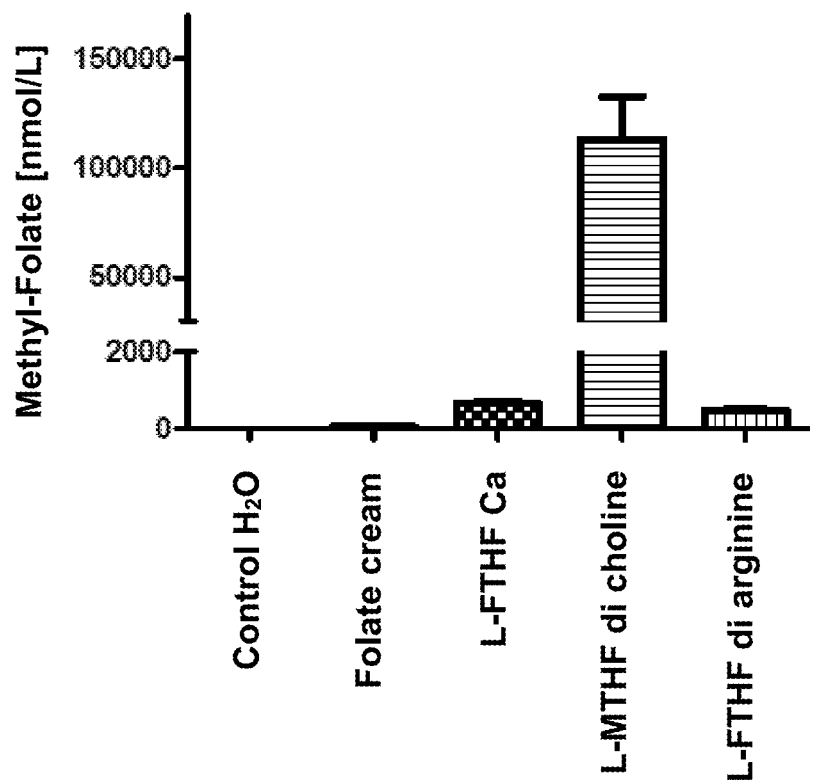
Figure 22:
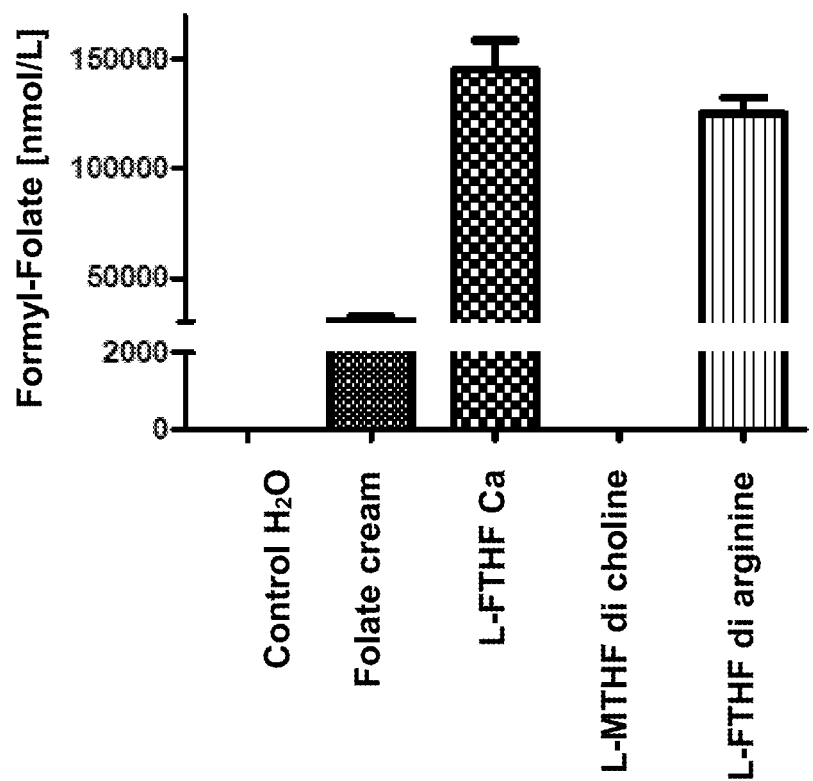

The methylfolate peak determined in the medium after incubation with L-MTHF di choline was outside the calibration line (FIGS. 9, 11, 13, 16 and 21). This also applies to the formylfolate concentrations after 24 h (FIGS. 14, 17 and 22). These peaks have nevertheless been interpolated, but their absolute values are considered uncertain. However, they can definitely be considered very high.

For some of the samples measured in the first analysis runs, the formyl folate content had not been considered (4 h and 24 h first round). Therefore, these samples have no formylfolate content data or just one-pass data.

Figure 8A:
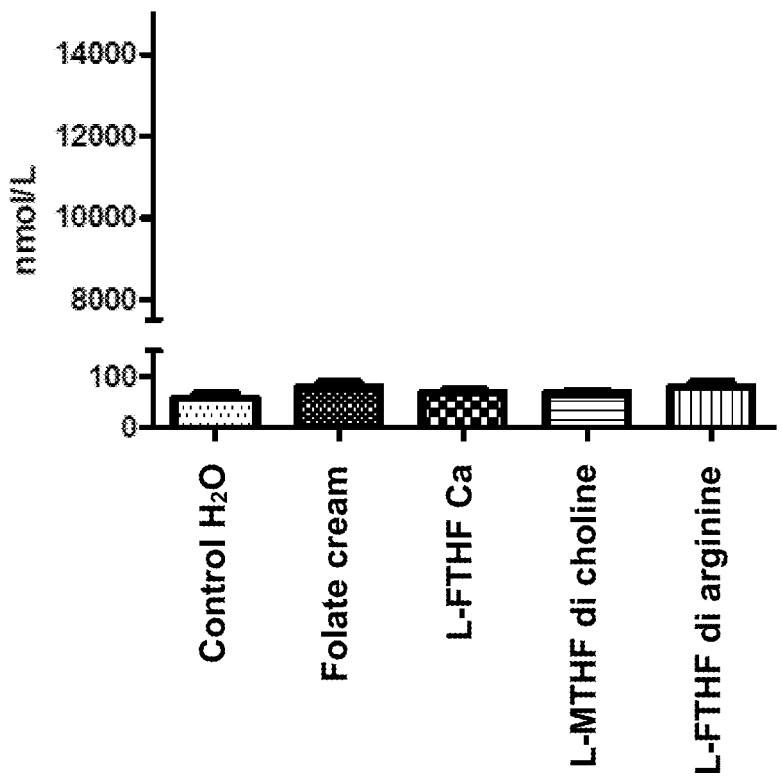
FIGS. 8 to 22 show results regarding bioavailability of folic acid, methyl-folate and formyl-folate in skin models at different time points.
Figure 8B:
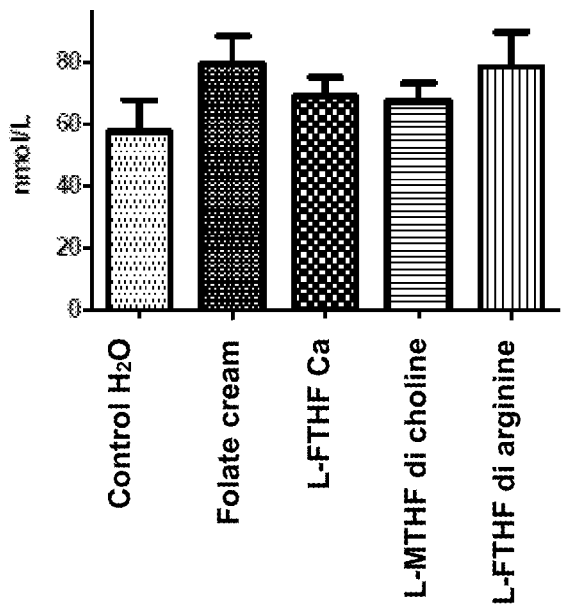
Figure 9:
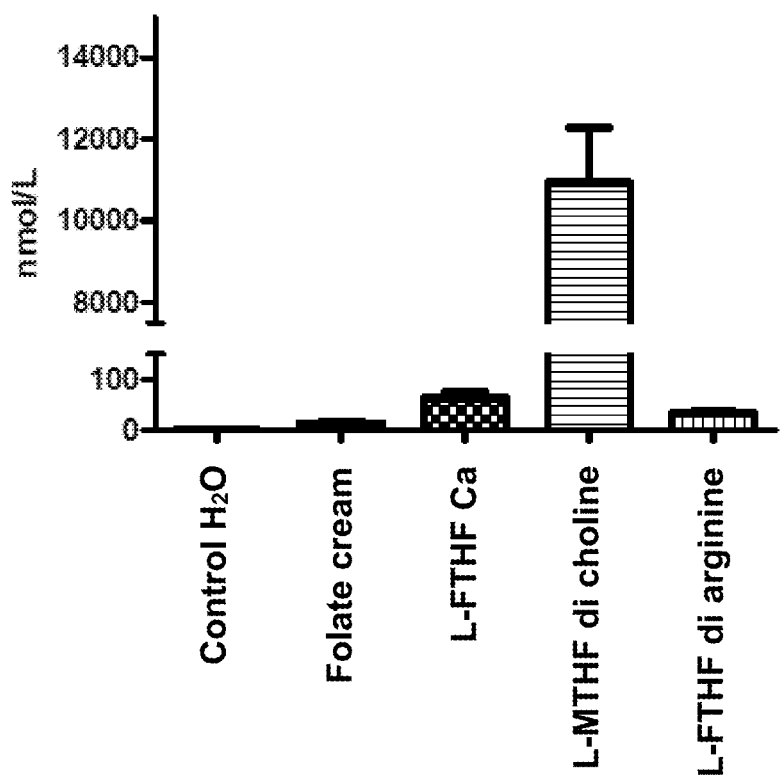

FIGS. 8A, 8B and 9 show the determination of folic acid or methylfolate concentrations in the compartment under skin models in the run. In the FIG. 8B the bars of FIG. 8A are displayed in a different scale. In each case 100 μL of the solutions were analyzed. N=3+SEM.

The skin models of the treatment groups hardly differ in terms of folic acid release. In contrast, large differences in methylfolate concentrations are measured among the models. Among the models supplemented with L-MTHF di choline, significantly higher concentrations were measured than in the models supplemented with L-FTHF or folate cream. The difference between the folic acid concentrations and the maximum measured methylfolate concentration is particularly large (FIG. 9).

Figure 10A:
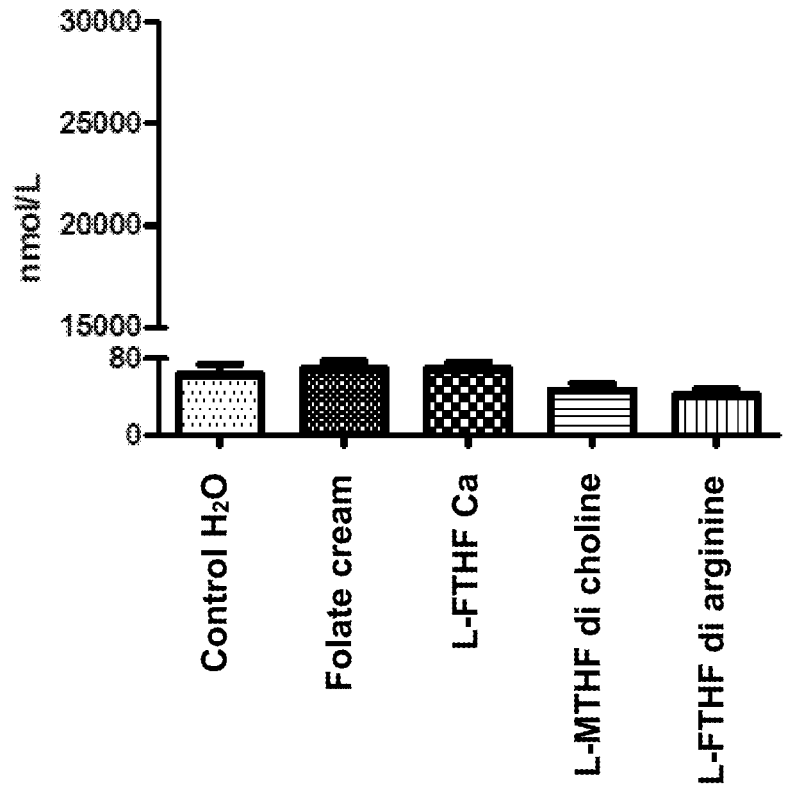
Figure 10B:
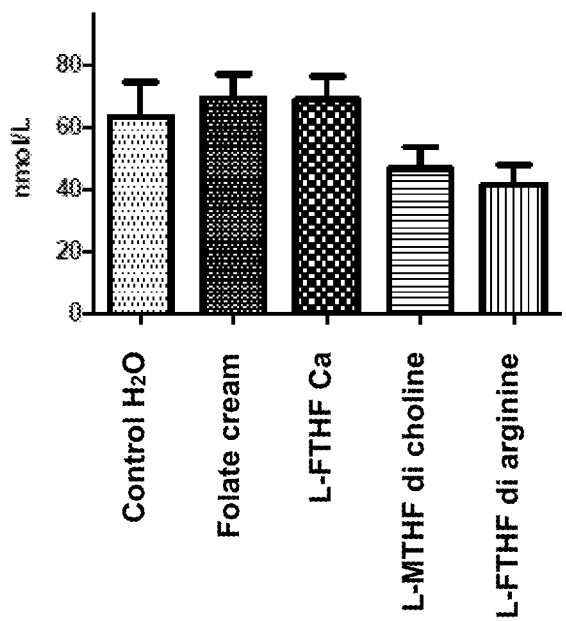
Figure 11:
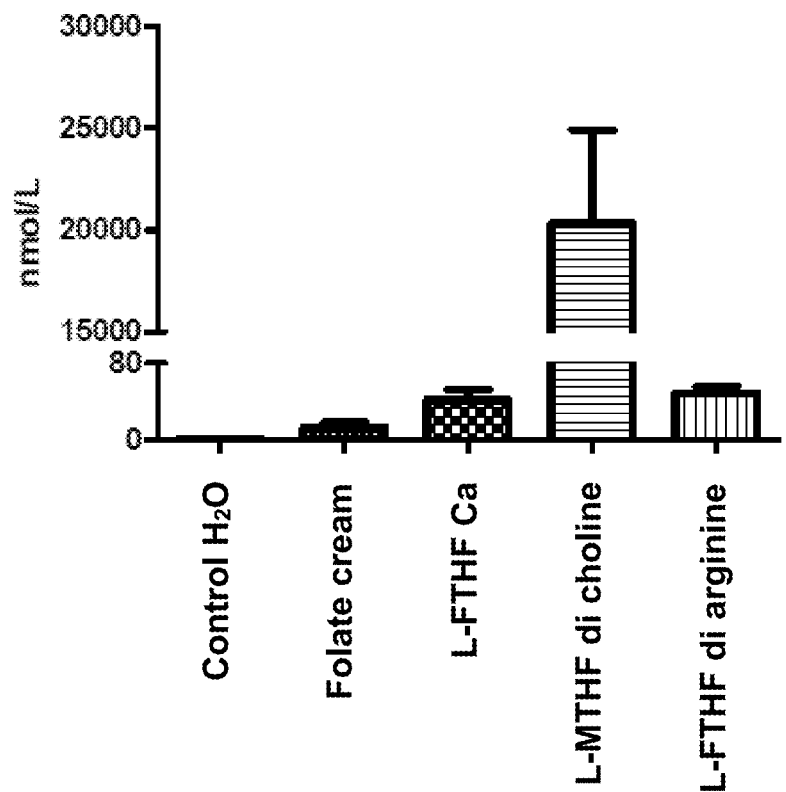
Figure 12A:
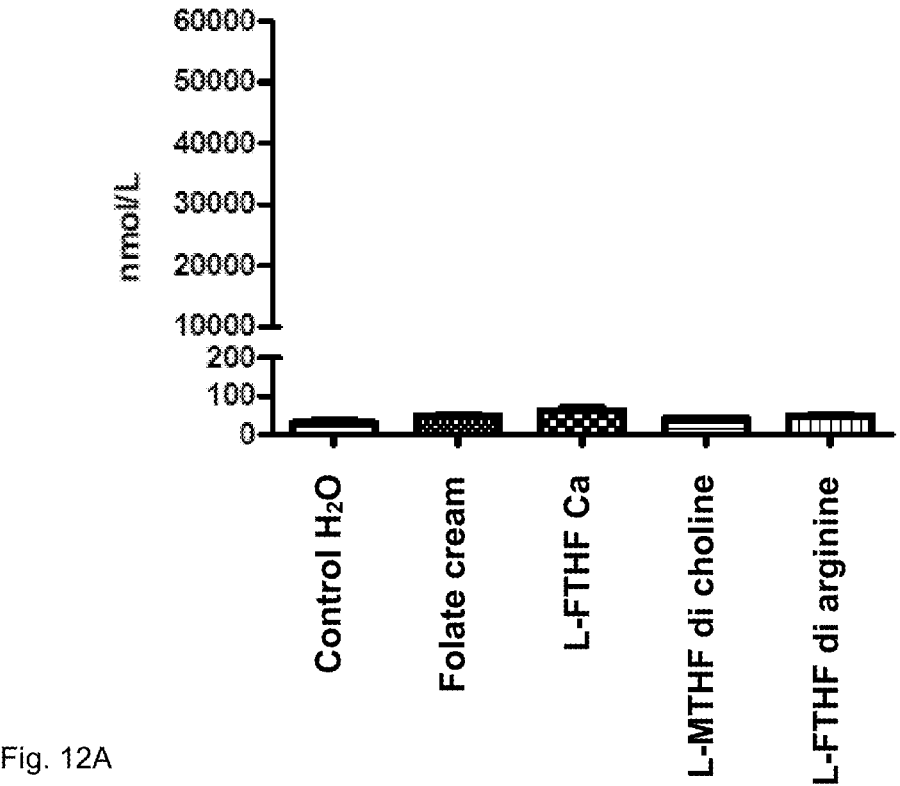
Figure 12B:
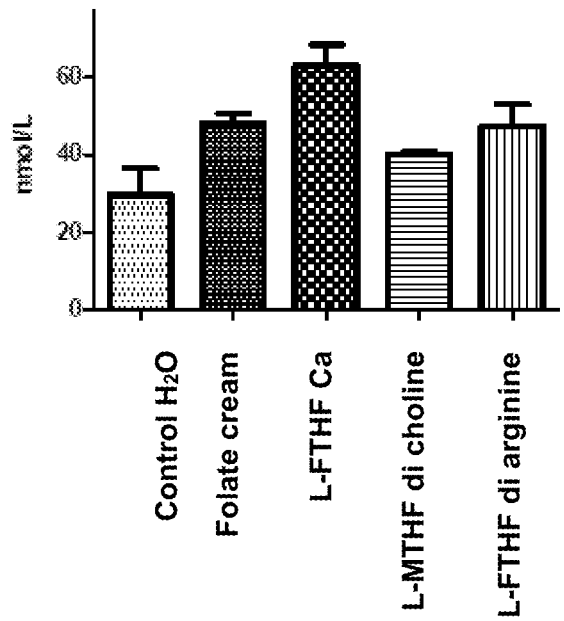

FIGS. 10A, 10B and 11 show the determination of folic acid or methylfolate concentrations in the compartment under the skin models in the second round. In each case 100 μl of the solutions were analyzed. N=3+SEM.

Both runs consistently show a very similar folic acid concentration in the compartment after 4 hours (FIGS. 8A, 8B and 10). Since the culture medium which contained the nutrient-supplied folic acid models prior to treatment with the test substances, it is assumed that the values determined here are in part still derived from residues of this medium which are gradually released from the cells, since more folates are topically offered. The folic acid concentrations among the models are relatively similar after 4 hours and thus obviously independent of the supplementation. The small differences shown (FIGS. 8A, 8B and 10A, 10B) are not significant (ANOVA over GraphPad Prism 5.04). In contrast, very different amounts of methylfolate in the buffer are found among the models after 4 h of treatment (FIGS. 9 and 11). On the basis of these results, the different bioavailability of the folic acid preparations can be read off. The folate cream is ten times less concentrated than the liquid products, but shows only six to seven times lower concentration of methylfolate in the recipient compartment.

The FIGS. 12A, 12B, 13 and 14 show the measurement of folic acid, methylfolate, formyl folate Concentrations in Skin Compartments After 8 h 1st run. In each case 100 μL of the solutions were analyzed. N=3+SEM.

FIGS. 15A, 15B, 16 and 17 show the determination of folic acid, methylfolate, formyl folate concentrations in the skin model after 8 h in the second run. In each case 100 μL of the solutions were analyzed. N=3+SEM.

After 8 h, the folic acid concentration in the skin model compartment barely rises above the 4 h values (FIGS. 12, 15 compared to FIGS. 8A, 8B and 10). In contrast, the methylfolate values at least partially show a clear increase (FIGS. 13 and 14). L-MTHF di choline causes the highest concentrations. The formylfolate concentration in the recipient compartment (basal), after supplementation with folate cream, L-FTHF Ca and L-FTHF di arginine (FIGS. 14 and 17), is similar to that of methylfolate after supplementation with L-MTHF di choline (FIGS. 13 and 17) 16). Formylfolate cannot be detected in the samples after L-MTHF. Formylfolate cannot be formed from methylfolate or only via energy-consuming metabolic pathways.

Figure 18A:
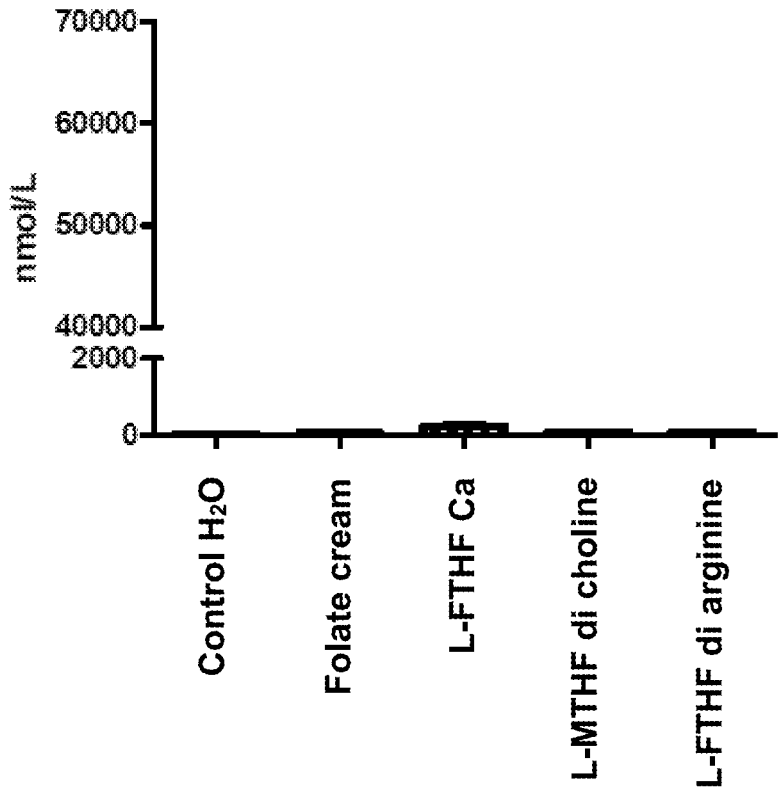
Figure 18B:
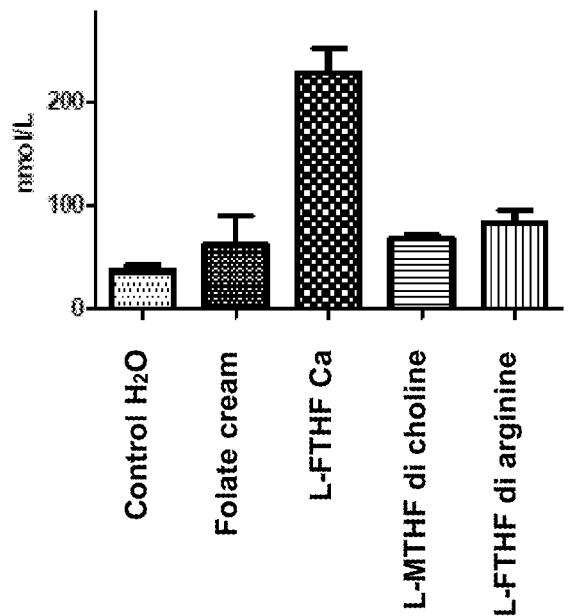
Figure 19:
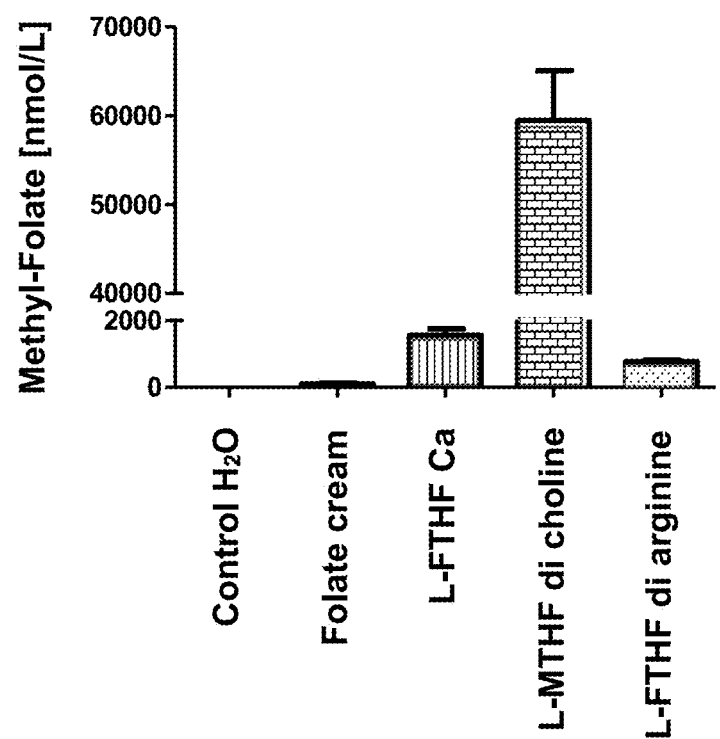
Figure 20A:
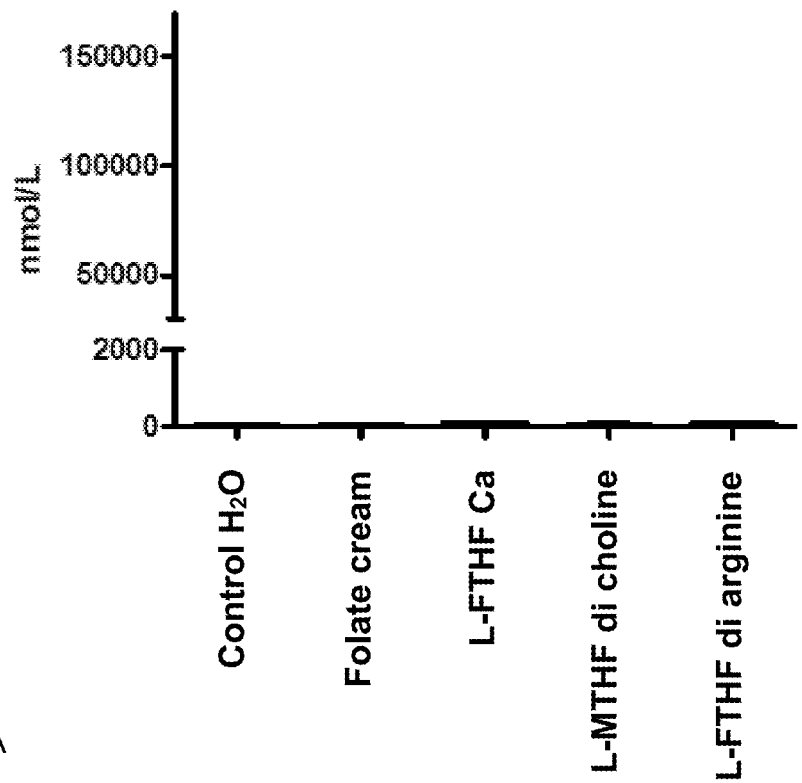
Figure 20B:
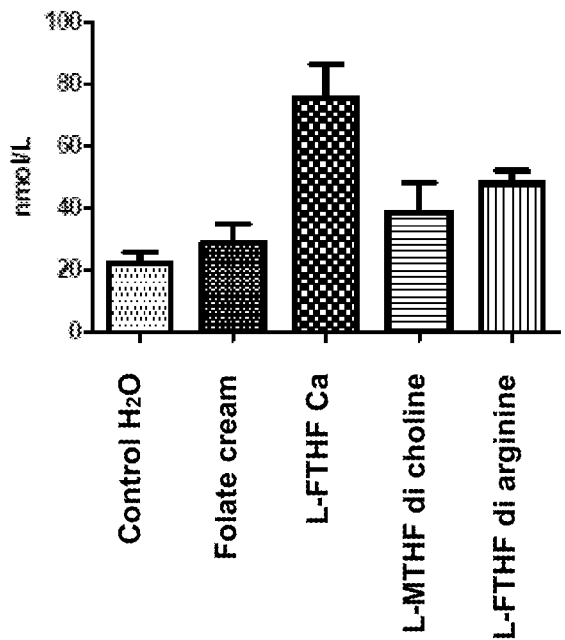

FIGS. 18A, 18B and 19 show the measurement of folic acid, methylfolate concentrations in the compartment under the skin models after 24 h in the first round. In each case 100 μL of the solutions were analyzed. N=3+SEM.

FIGS. 20A, 20B, 21, and 22 show the determination of folic acid, methylfolate, formylfolate concentrations in the skin model compartment after 24 hours in the second round. In each case 100 μL of the solutions were analyzed. N=3+SEM.

After 24 h (graphs 18A, 18B, 20A, and 20B) both the folic acid (partially) and methylfolate concentrations are higher than after 4 h and 8 h. The folic acid concentrations among the skin models which were treated with L-FTHF Ca are twice as high as the concentrations among the other skin models, which in turn are similar. However, the folic acid concentration is negligible compared to the measured methylfolate and formylfolate concentrations. The differences at the level of methylfolate are very high (FIGS. 19 and 21). The peaks from the samples under L-MTHF were significantly higher than the highest standard. Also, relatively high is the concentration of methylfolate among models treated with L-FTHF Ca. The concentration of the solution among the models treated with L-FTHF di arginine is approximately half that and the folate cream produces the lowest values (out of control) at 108 nmol/L. The concentrations are again significantly higher than after 4 h (folate cream approx. 3 nmol/L) (FIGS. 19 and 21). Formylfolate cannot be detected in the samples after L-MTHF di choline since formylfolate cannot be formed from methylfolate or only through energy-consuming metabolic pathways (FIG. 22). On the other hand, it is easily measurable in all other samples (with the exception of the control).

At the beginning of the bioavailability studies, 50 μl of the solutions (25 mg/ml or 60 mmol/l) and of the cream (2.5 mg/ml or 6 mmol/L) applied. In the lower compartment, 1 mL each of HBSS was initially charged. The results shown in the figures mentioned above were determined from 100 μL aliquots of this buffer amount.

In the apical compartment, 3 μmol of folate (solutions) or 0.3 μmol of folate are supplemented (in 50 μL).

In the basal compartment after 24 h supplementation with L-FTHF Calcium maximum about 200 nmol/L folate. Of the folate cream 29 nmol/L were determined after 24 h supplementation.

Methylfolate was measured at a maximum of 120 μmol/L (24 h L-MTHF) Of the folate cream 47 nmol/L were determined after 24 h supplementation.

Formylfolate was measured at a maximum of 150 μmol/L (24 h L-FTHF Ca.) Of the folate cream 30.21 μmol/L were measured at this time.

Supplementation with various folate preparations led to significantly accelerated regeneration of an artificial wound after 24 h in the scratch assay. This study was performed in monolayer cell lawn of primary epithelial cells as compared to the untreated control.

The bioavailability of methylfolate or formylfolate from the preparations could be demonstrated after supplementation of reconstructed skin models. The topically offered folate derivatives be transported through the fabric of the models and partially metabolized by the cells. Part of the topically offered formylfolate is metabolized to methylfolate, another part is transported through the tissue. Conversely, the topically offered methyl formate as such is transported through the tissue of the skin models and not metabolized to formylfolate. The effectiveness of the uptake, which was documented as transport, is twice as good from the folate cream in terms of formylfolate than from the pure folate solutions (L-FTHF Ca). Folic acid was also determined in the basal compartments of the skin models. However, the measured concentrations were far below those for methyl or formylfolate. Thus, the measured folic acid likely comes from the medium that was used for the growth of the skin models and is again released by the cells in the course of the experiments.

EXAMPLE 4

In a further experiment it was examined if calcium levoleucovorin is able to penetrate skin. Penetration depth was determined by way of Raman spectroscopy. The measurement device was an inverse Raman microscope model 3510 with 60× oil immersion lens and evaluation software SkinTools of the company RiverD Rotterdam and the method were 10 profiles per application, measuring time of 5 seconds per measuring point, 7 steps of 2 μm, 4 steps of 4 μm, spectral range of 400-1800 cm$^{-1}$, at a laser excitation wavelength of 785 nm. Signals were generated with the software SkinTools that contains various skin and device specific spectra. The user can add their own spectra to the library. The evaluation is carried out via the CLS procedure (least squares method). The signals are output as a fit coefficient normalized to the fit coefficient of keratin.

For a quantitative indication of the result, a calibration must be carried out with standard series (see Tab. 1 and Tab. 2). First, the sensitivity of bovine serum albumin (BSA) is determined and the mass concentration BSA in g/ml is plotted against the BSA fit coefficient. A linear regression with fixed zero gives slope S. For the active substance, the molar concentration in mmol/ml is plotted against the drug coefficient multiplied by the BSA fit coefficient. This gives the slopes SA of the active ingredient. With the slopes, a so-called quantification factor of the drug can be created ($S_A/S=C$). Multiplied by the factor C, the coefficient of fit of the active substance becomes the quantified value with the unit mmol/g of keratin.

The standard series for determining the sensitivity of the analysis system to keratin was:

Tab 1

| Standard | BSA (g/ml) |
|---|---|
| Std0 | 0.0000 |
| Std1 | 0.0201 |
| Std2 | 0.0409 |
| Std3 | 0.0600 |

The standard series for determining the quantification coefficient of calcium levoleucovorin:

Tab 2

| Standard | Calcium levoleucovorin (mmol/ml) |
|---|---|
| Std0 | 0.0000 |
| Std1 | 0.0050 |
| Std2 | 0.0098 |
| Std3 | 0.0147 |

The application of the drug or placebo (sodium gluconate) to the skin of a subject was done as follows: 20 μL was pipetted into an allergy patch and this was then stuck onto the forearm of a subject for a period of 30, 60, 120 and 240 minutes. At the end of the application time, the allergy patch was removed. Prior to determining the Raman profiles, the treated skin area was rubbed with a dry paper towel.

The determined fit coefficients fi and quantification factors Ci are listed in the tables below:

| Standard | $f_{BSA}$ | $f_{Ca\text{-}Levoleucovorin} f_{BSA}$ |
|---|---|---|
| Std0 | $-3.36 \times 10^{-6}$ | $-3.45 \times 10^{-2}$ |
| Std1 | $3.75 \times 10^{-5}$ | $2.46 \times 10^{-1}$ |
| Std2 | $9.36 \times 10^{-5}$ | $4.65 \times 10^{-1}$ |
| Std3 | $1.25 \times 10^{-4}$ | $7.02 \times 10^{-1}$ |

Slope S of BSA and slope SA and the quantification coefficient Ci of the active substances:

| substance | Slope S | Slope $S_A$ | $C_i$ |
|---|---|---|---|
| BSA | 468.67 | | |
| Ca-Levoleucovorin | | 0.0209 | $4.46 \times 10^{-5}$ |

Figure 23:
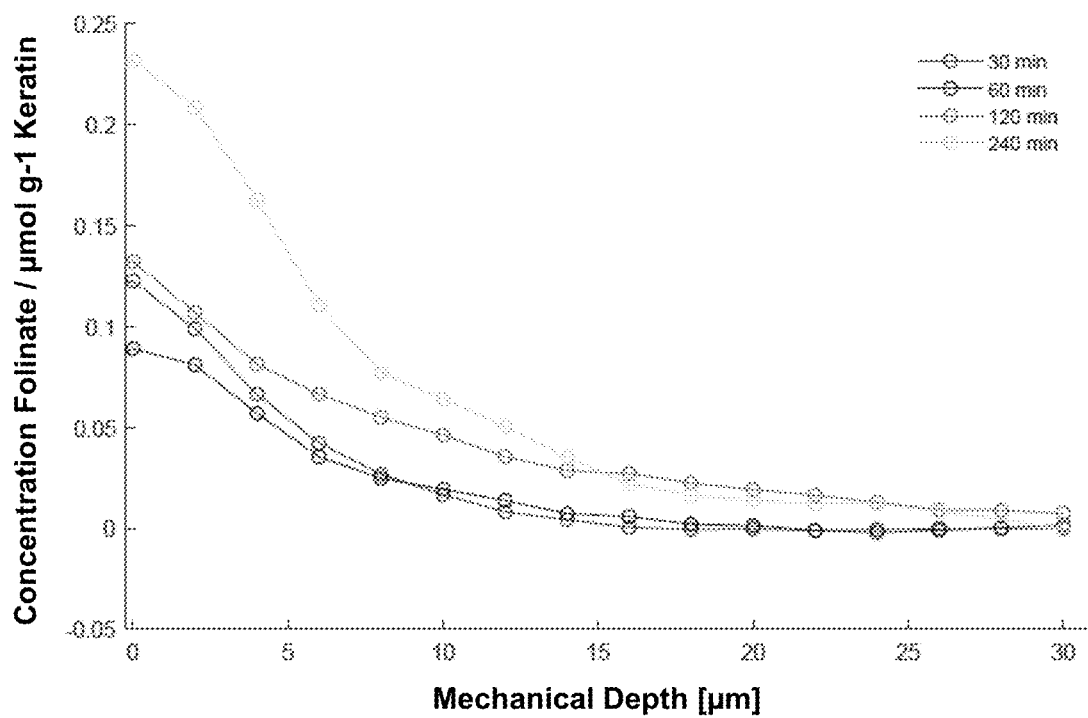
FIG. 23 shows results regarding the penetration of folinate in human skin.

FIG. 23 shows the calcium levoleucovorin profiles for 30 to 240 Minutes application time. There is a tendency to increased calcium levoleucovorin concentration both in the top 5 μm and deeper layers of the skin. The standard deviation—not shown here—of the individual profiles are however large.

The table below shows the determined active substance contents per area, which are penetrated into the skin. The profiles were evaluated from the skin surface to a depth of 30 μm. There is a tendency to increase calcium levoleucovorin concentration over time. The proportion of active ingredient in the skin compared to the applied amount is at an application time of 240 minutes at 10%:

| Application period (min.) | Calcium levoleucovorin (μmol/cm²) | Amount recovered (% of amount applied) |
|---|---|---|
| 30 | 0.37 +/− 0.27 | 3.76 +/− 2.82 |
| 60 | 0.32 +/− 0.25 | 3.28 +/− 2.58 |
| 120 | 0.62 +/− 0.8 | 6.3 +/− 8.22 |
| 240 | 0.97 +/− 0.32 | 9.96 +/− 3.26 |

EXAMPLE 5

Figure 24:
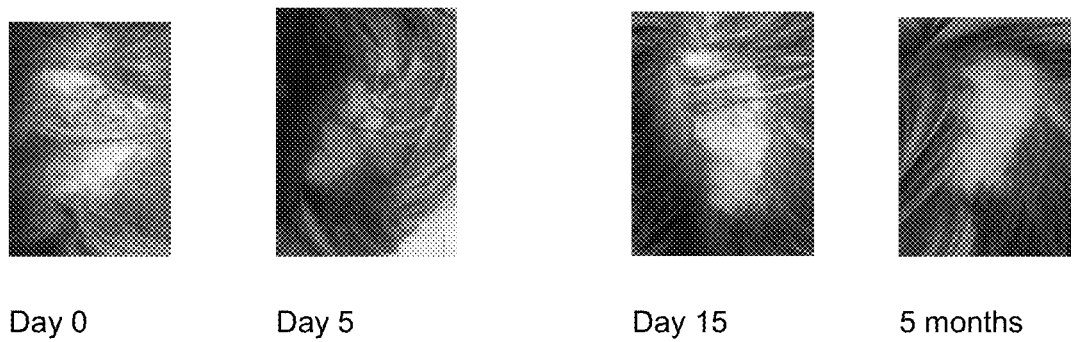
FIG. 24 shows the course of a treatment of a patient with a skin disorder with folate cream.
Figure 24:
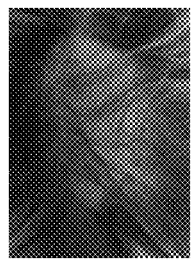

The folate comprising cream described in example 1 was used in the treatment of 5 patients suffering from different skin problems, i.e. neurodermitis and psoriasis. Symptoms massively decreased in the course of the treatment over up to 21 days. One patient has been suffering from Folliculitis decalvans who had been conventionally treated for several years. Treatment with the folate cream over a period of 3 weeks led to an almost complete regression of the symptoms and healing of the skin as shown in FIG. 24. Up to a period of 9 months no relapse occurred, and the skin kept its normal appearance.

A child suffering from neurodermitis was treated with a folate preparation according to the present invention over a period of three weeks. The symptoms decreased during the treatment and the skin healed completely. No relapse occurred after the treatment had been stopped.

The invention claimed is:

1. A method of treating epithelial tissue irritations and disorders, comprising topically administering a preparation comprising at least one folate salt to a patient in need thereof, wherein the folate salt comprises an anion selected from the group consisting of 5-formyl-(6RS)-tetrahydrofolic acid, 5-formyl-(6S)-tetrahydrofolic acid, 10-formyl-(6R)-tetrahydrofolic acid, 5-methyl-(6RS)-tetrahydrofolic acid, 5-methyl-(6S)-tetrahydrofolic acid, (6S)-tetrahydrofolic acid, 5,10-methylene-(6R)-tetrahydrofolic acid, 5-methyl-10-formyl-(6S)-tetrahydrofolic acid, and 5,10-diformyl-(6S)-tetrahydrofolic acid.

2. The method of claim 1, wherein the epithelial tissue is skin.

3. The method of claim 2, wherein the skin disorder is an inflammatory skin disorder.

4. The method of claim 2, wherein the skin disorder is psoriasis.

5. The method of claim 2, wherein the skin disorder is dermatitis or neurodermitis.

6. The method of claim 2, wherein the skin disorder is a chronic wound.

7. A folate preparation for use in the method of any of claims 1-6, comprising:
a physiologically effective amount of at the least one folate salt having a cation selected from the group consisting of arginine, choline, acetylcholine, 1,1-dimethylbiguanidine, phenylethylbiguanidine, glucosamine, and dimethylaminoethanol; and
one or more customary compounds for forming a support matrix.

8. The folate preparation according to claim 7, having a concentration of 0.01 weight-% to 2.5 weight-% folate salt based on the total weight of the folate preparation, the preparation being in the form of a microemulsion, an oil in water emulsion, a water in oil emulsion, a nanoparticle formulation, a gel formulation, or a spray formulation.

9. The folate preparation of claim 7, comprising a phase A, a phase B, a phase C, and an optional phase D, wherein
phase A comprises an oil,
phase B comprises glycerol and an emulsifier,
phase C comprises the at least one folate salt in a physiologically effective amount, and
optional phase D comprises a matting agent.

10. The folate preparation according to claim 7, further comprising at least one additional compound selected from the group consisting of arginine, arginine ester, choline, acetylcholine, glucosamine, dimethylaminoethanol, vitamins of the B complex, and vitamin D.

11. The folate preparation according to claim 9, wherein the phase C comprises a polar solvent and 0.1 to 1000 mg of the cation of the of the folate salt per milliliter polar solvent.

12. The folate preparation according to claim 7, further comprising at least one compound selected from the group consisting of sodium gluconate, potassium gluconate, glycerophosphate disodium salt, and glycerophosphate dipotassium salt.

13. The folate preparation according to claim 9, wherein the oil of phase A comprises a medium-chain triglycerol, wherein the fatty acids have a chain length in the range of $C_6$ to $C_{12}$ and optionally comprises a dicarbonic acid alcohol, wherein the dicarbonic acid has a chain length in the range of $C_2$ to $C_{10}$ and the alcohol is selected of the group consisting of methyl, ethyl, isopropyl, propyl, butyl, pentyl alcohol.

14. The folate preparation according to claim 13, wherein the oil is caprylic/capric acid triglycerol.

15. The folate preparation according to claim 9, wherein the emulsifier of phase B has a HLB value equal or greater than 5.

16. The folate preparation according to claim 15, wherein the emulsifier is a sucrose ester with saturated fatty acids having a chain length in the range of $C_{14}$ to $C_{20}$.

17. A method of treating skin irritations and skin disorders, comprising administering to a patient in need of said treatment a folate preparation comprising a folate salt and a gluconate salt or a glycerophosphate salt, wherein the gluconate salt or the glycerophosphate salt acts as a permeation enhancer for the folate salt into the skin, wherein the folate salt comprises an anion selected from the group consisting of 5-formyl-(6RS)-tetrahydrofolic acid, 5-formyl-(6S)-tetrahydrofolic acid, 10-formyl-(6R)-tetrahydrofolic acid, 5-methyl-(6RS)-tetrahydrofolic acid, 5-methyl-(6S)-tetrahydrofolic acid, (6S)-tetrahydrofolic acid, 5,10-methylene-(6R)-tetrahydrofolic acid, 5-methyl-10-formyl-(6S)-tetrahydrofolic acid, and 5,10-diformyl-(6S)-tetrahydrofolic acid.

18. The folate preparation according to claim 16, wherein the sucrose ester comprises a sucrose stearate.

19. A folate preparation for use in the method of any of claims 1-6, wherein the at least one folate salt comprises a cation selected from the group consisting of calcium, sodium, and mixtures thereof.

* * * * *

UNITED STATES PATENT AND TRADEMARK OFFICE
CERTIFICATE OF CORRECTION

PATENT NO. : 12,138,266 B2
APPLICATION NO. : 17/256456
DATED : November 12, 2024
INVENTOR(S) : Martin Ulmann, Gerd Wiesler and Hans Dutler Page 1 of 1

It is certified that error appears in the above-identified patent and that said Letters Patent is hereby corrected as shown below:

In the Claims

Claim 7, Column 13, Line 53, delete "at the least" and insert --the at least--
Claim 11, Column 14, Line 19, delete the first occurrence of "of the"

Signed and Sealed this
Eighteenth Day of March, 2025

Coke Morgan Stewart
*Acting Director of the United States Patent and Trademark Office*